(12) United States Patent
Fougere et al.

(10) Patent No.: US 9,022,961 B2
(45) Date of Patent: May 5, 2015

(54) ORAL CARE CLEANING AND TREATING DEVICE

(75) Inventors: Richard J. Fougere, Washington Crossing, PA (US); Robert W. Fusi, II, Flemington, NJ (US); Justin E. McDonough, Flemington, NJ (US)

(73) Assignee: McNeil-PPC., Inc., Skillman, NJ (US)

( * ) Notice: Subject to any disclaimer, the term of this patent is extended or adjusted under 35 U.S.C. 154(b) by 728 days.

(21) Appl. No.: 13/314,263

(22) Filed: Dec. 8, 2011

(65) Prior Publication Data
US 2012/0077144 A1 Mar. 29, 2012

Related U.S. Application Data

(63) Continuation-in-part of application No. 12/844,875, filed on Jul. 28, 2010, now Pat. No. 8,684,956, and a continuation-in-part of application No. 12/844,879, filed on Jul. 28, 2010, now Pat. No. 8,617,090, and a continuation-in-part of application No. 12/844,883, filed on Jul. 28, 2010, and a continuation-in-part of application No. 12/844,885, filed on Jul. 28, 2010.

(60) Provisional application No. 61/229,839, filed on Jul. 30, 2009.

(51) Int. Cl.
*A61C 17/02* (2006.01)
*A46B 9/04* (2006.01)

(52) U.S. Cl.
CPC ............. *A46B 9/045* (2013.01); *A61C 17/0211* (2013.01); *A61C 17/0217* (2013.01)

(58) Field of Classification Search
USPC ................ 601/160, 162, 163, 164, 165, 139; 433/71, 80, 81, 88, 91, 216; 15/22.1, 15/167.1, 167.2, 172, 176.1
See application file for complete search history.

(56) References Cited

U.S. PATENT DOCUMENTS

| | | |
|---|---|---|
| 1,500,107 A | 7/1924 | Chandler |
| 3,516,402 A | 6/1970 | Toth |
| 3,566,869 A | 3/1971 | Crowson |
| 3,731,675 A | 5/1973 | Kelly |
| 3,840,992 A | 10/1974 | English |
| 4,017,373 A | 4/1977 | Shaw |
| 4,071,956 A | 2/1978 | Andress |
| 4,106,501 A | 8/1978 | Ozbey et al. |
| 4,148,309 A | 4/1979 | Reibel |
| 4,164,940 A | 8/1979 | Quinby |
| 4,170,230 A | 10/1979 | Nelson |
| 4,237,574 A | 12/1980 | Kelly et al. |
| 4,291,017 A | 9/1981 | Beierle et al. |

(Continued)

FOREIGN PATENT DOCUMENTS

| | | |
|---|---|---|
| CN | 2356653 | 1/2000 |
| CN | 103327931 A | 9/2013 |

(Continued)

*Primary Examiner* — Quang D Thanh

(57) ABSTRACT

A device for directing a liquid onto a plurality of surfaces of the oral cavity, the device including a handle, a neck, and a head, where the head includes a cleaning component including a chamber for maintaining the liquid proximate the surfaces, where the chamber is defined by front and rear sealing membranes, inner side walls and a base inner wall, and where the inner side walls each include a plurality of openings, the device further including a first manifold and a second manifold, and a first port and a second port for conveying liquid.

8 Claims, 15 Drawing Sheets

(56) References Cited

U.S. PATENT DOCUMENTS

| | | |
|---|---|---|
| 5,029,576 A | 7/1991 | Evans, Sr. |
| 5,030,098 A | 7/1991 | Branford |
| 5,046,491 A | 9/1991 | Derrick |
| 5,104,315 A | 4/1992 | McKinley |
| 5,137,039 A | 8/1992 | Klinkhammer |
| 5,177,827 A | 1/1993 | Ellison |
| 5,355,893 A | 10/1994 | Mick |
| 5,365,624 A | 11/1994 | Berns |
| 5,443,386 A | 8/1995 | Viskup |
| 5,458,487 A | 10/1995 | Komatsu |
| 5,509,801 A | 4/1996 | Nicholson |
| 5,570,709 A | 11/1996 | Haddad et al. |
| 5,616,028 A | 4/1997 | Hafele et al. |
| 5,950,624 A | 9/1999 | Hart |
| 5,980,498 A | 11/1999 | Brown |
| 6,022,326 A | 2/2000 | Tatum |
| 6,126,444 A | 10/2000 | Horiguchi |
| 6,152,733 A | 11/2000 | Hegemann et al. |
| 6,155,824 A | 12/2000 | Kamen et al. |
| 6,174,164 B1 | 1/2001 | Masjedi |
| 6,203,320 B1 | 3/2001 | Williams et al. |
| 6,224,376 B1 | 5/2001 | Cloonan |
| 6,353,956 B1 | 3/2002 | Berge |
| 6,602,071 B1 | 8/2003 | Ellion et al. |
| 6,893,259 B1 | 5/2005 | Reizenson |
| 6,935,857 B1 | 8/2005 | Farrell |
| 7,118,377 B2 | 10/2006 | Inoue |
| 7,364,551 B2 | 4/2008 | Allen |
| 7,935,065 B2 | 5/2011 | Martin |
| 7,972,277 B2 | 7/2011 | Oki |
| 8,684,956 B2 * | 4/2014 | McDonough et al. ........ 601/164 |
| 2002/0082544 A1 | 6/2002 | Thrash et al. |
| 2003/0143511 A1 | 7/2003 | Trichas |
| 2003/0153844 A1 | 8/2003 | Smith |
| 2003/0233086 A1 | 12/2003 | Burns |
| 2004/0045107 A1 | 3/2004 | Egeresi |
| 2004/0082878 A1 | 4/2004 | Baldwin |
| 2004/0087874 A1 | 5/2004 | Schneider |
| 2004/0106081 A1 | 6/2004 | Karazivan et al. |
| 2004/0146836 A1 | 7/2004 | Andersen |
| 2004/0193235 A1 | 9/2004 | Altshuler et al. |
| 2005/0037315 A1 | 2/2005 | Inoue et al. |
| 2005/0096563 A1 | 5/2005 | Liang |
| 2005/0136376 A1 | 6/2005 | Yeh |
| 2005/0196725 A1 | 9/2005 | Fu |
| 2005/0272002 A1 | 12/2005 | Chenvainu et al. |
| 2006/0078844 A1 | 4/2006 | Goldman et al. |
| 2006/0188841 A1 | 8/2006 | Edel et al. |
| 2007/0106138 A1 | 5/2007 | Beiski |
| 2007/0140777 A1 | 6/2007 | Brunson |
| 2007/0169295 A1 * | 7/2007 | Winter et al. ................ 15/167.2 |
| 2007/0184404 A1 | 8/2007 | Johnki |
| 2007/0254260 A1 | 11/2007 | Alden |
| 2008/0131844 A1 * | 6/2008 | Taylor ......................... 433/216 |
| 2008/0182218 A1 | 7/2008 | Chen |
| 2008/0199831 A1 | 8/2008 | Teichert et al. |
| 2008/0280251 A1 | 11/2008 | Gallagher |
| 2009/0123886 A1 | 5/2009 | Vaska |
| 2009/0136893 A1 | 5/2009 | Zegarelli |
| 2009/0208898 A1 | 8/2009 | Kaplan |
| 2010/0004555 A1 | 1/2010 | Bazemore |
| 2010/0016908 A1 | 1/2010 | Martin |
| 2010/0081954 A1 | 4/2010 | Hyde |
| 2010/0242193 A1 | 9/2010 | Harrison et al. |
| 2010/0311007 A1 | 12/2010 | Eliyahov |
| 2010/0312133 A1 | 12/2010 | Bazemore |
| 2010/0330538 A1 | 12/2010 | Salazar |
| 2011/0015543 A1 | 1/2011 | Butlin |
| 2011/0021942 A1 | 1/2011 | Choe |
| 2011/0113576 A1 * | 5/2011 | Yankell ........................ 15/167.2 |
| 2011/0213228 A1 | 9/2011 | Martin |
| 2011/0294096 A1 | 12/2011 | DeCastro et al. |
| 2011/0318705 A1 | 12/2011 | Sullivan |
| 2012/0077143 A1 * | 3/2012 | Fougere et al. ................ 433/82 |
| 2012/0123225 A1 | 5/2012 | Al-Tawil |
| 2012/0219926 A1 | 8/2012 | Sullivan et al. |
| 2013/0023797 A1 | 1/2013 | Hanewinkel |
| 2013/0211270 A1 | 8/2013 | St. Laurent |

FOREIGN PATENT DOCUMENTS

| | | |
|---|---|---|
| EP | 101618 A | 2/1984 |
| EP | 688542 A | 12/1995 |
| EP | 761181 A | 3/1997 |
| EP | 1525857 A | 4/2005 |
| FR | 2455456 A | 11/1980 |
| JP | 59125556 A | 7/1984 |
| JP | 2299651 A | 12/1990 |
| JP | 6217996 A | 8/1994 |
| JP | 7047088 A | 2/1995 |
| JP | 11035435 A | 2/1999 |
| JP | 11309160 A | 11/1999 |
| JP | 2001-008736 A | 1/2001 |
| JP | 2001-120579 A | 5/2001 |
| JP | 2001-120627 A | 5/2001 |
| JP | 2002-045378 A | 2/2002 |
| JP | 2004-057315 A | 2/2004 |
| JP | 2004-230118 A | 8/2004 |
| JP | 2005-319254 A | 11/2005 |
| JP | 2005-334104 A | 12/2005 |
| JP | 2006-101941 A | 4/2006 |
| JP | 2006-239368 A | 9/2006 |
| JP | 2008501412 A | 1/2008 |
| JP | 2008515575 | 5/2008 |
| WO | WO 01/97709 A | 12/2001 |
| WO | WO 0197709 A1 | 12/2001 |
| WO | WO 03/039392 A | 5/2003 |
| WO | WO 2004/064666 A | 8/2004 |
| WO | WO 2004/108008 A | 12/2004 |
| WO | WO 2005/087133 A | 9/2005 |
| WO | WO 2005/107636 A | 11/2005 |
| WO | WO 2005120387 A2 | 12/2005 |
| WO | WO 2006040018 A1 | 4/2006 |
| WO | WO 2006100452 A1 | 9/2006 |
| WO | WO 2006/119855 A | 11/2006 |
| WO | WO 2006/128021 A | 11/2006 |
| WO | WO 2007/071031 A | 6/2007 |
| WO | WO 2007/121760 A | 11/2007 |
| WO | WO 2008/016342 A | 2/2008 |
| WO | WO 2012/018555 A8 | 2/2012 |

* cited by examiner

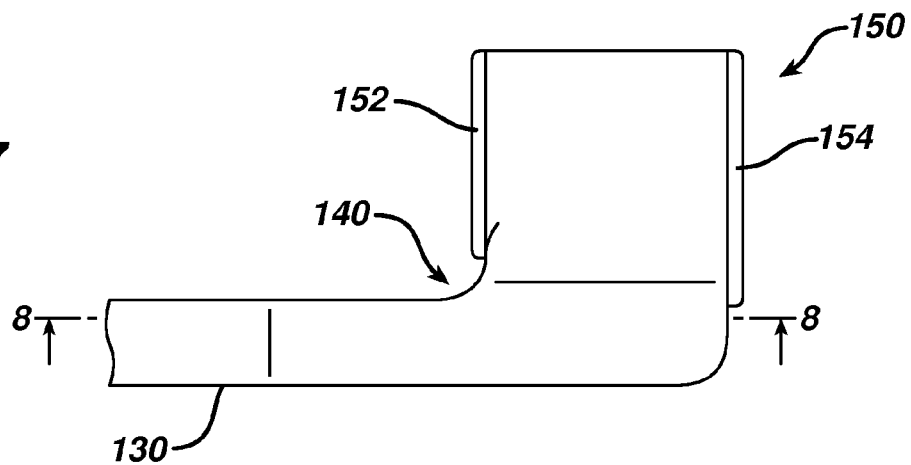
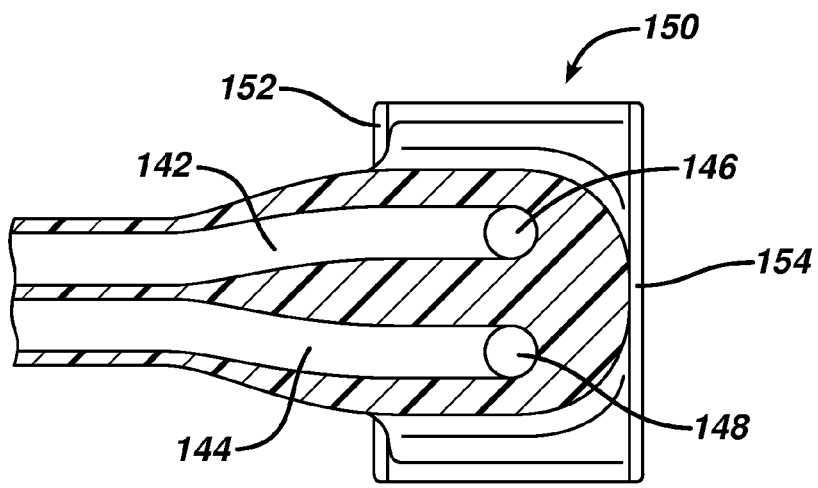
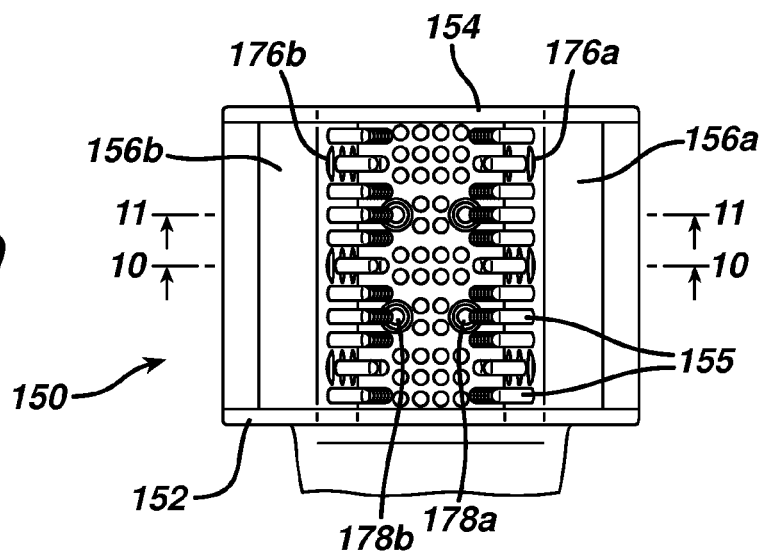

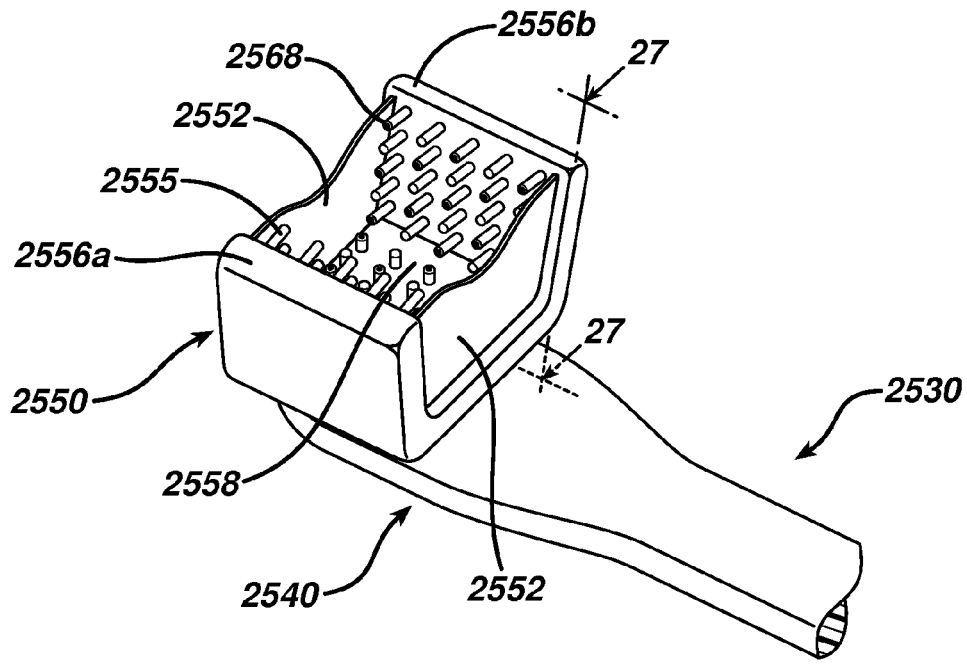
FIG. 21
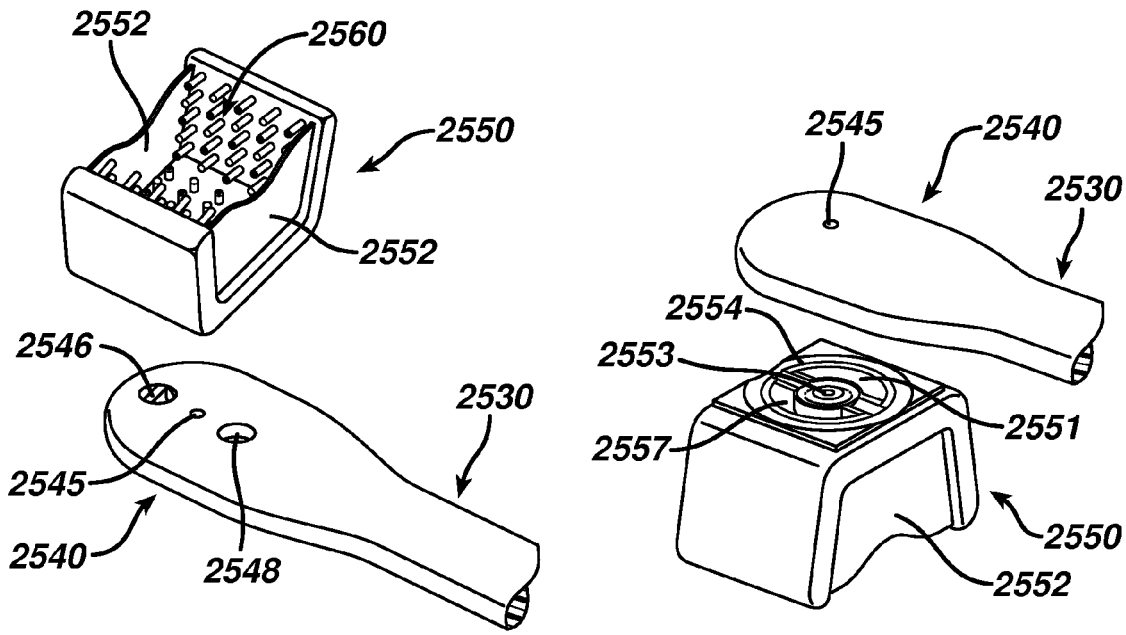
FIG. 22
FIG. 23

ORAL CARE CLEANING AND TREATING DEVICE

This application is a continuation-in-part of U.S. application Ser. No. 12/844,875, filed Jul. 28, 2010 now U.S. Pat. No. 8,684,956, a continuation-in-part of U.S. application Ser. No. 12/844,879, filed Jul. 28, 2010 now U.S. Pat. No. 8,617,090, a continuation-in-part of U.S. application Ser. No. 12/844,883, filed Jul. 28, 2010, and a continuation-in-part of U.S. application Ser. No. 12/844,885, filed Jul. 28, 2010, which claim the benefit of U.S. provisional application 61/229,839 filed Jul. 30, 2009, the complete disclosures each of which are hereby incorporated herein by reference for all purposes.

FIELD OF THE INVENTION

The present invention relates to oral care devices suitable for in-home use to provide a beneficial effect to the oral cavity of a mammal.

BACKGROUND OF THE INVENTION

In addition to regular professional dental checkups, daily oral hygiene is generally recognized as an effective preventative measure against the onset, development, and/or exacerbation of periodontal disease, gingivitis and/or tooth decay. Unfortunately, however, even the most meticulous individuals dedicated to thorough brushing and flossing practices often fail to reach, loosen and remove deep-gum and/or deep inter-dental food particulate, plaque or biofilm. Most individuals have professional dental cleanings biannually to remove tarter deposits.

For many years products have been devised to facilitate the simple home cleaning of teeth, although as yet a single device which is simple to use and cleans all surfaces of a tooth and/or the gingival or sub-gingival areas simultaneously is not available. The conventional toothbrush is widely utilized, although it requires a significant input of energy to be effective and, furthermore, a conventional toothbrush cannot adequately clean the inter-proximal areas of the teeth. Cleaning of the areas between teeth currently requires the use of floss, pick, or some such other additional device apart from a toothbrush.

Electric toothbrushes have achieved significant popularity and, although these reduce the energy input required to utilize a toothbrush, they are still inadequate to ensure proper inter-proximal tooth cleaning. Oral irrigators are known to clean the inter-proximal area between teeth. However, such devices have a single jet which must be directed at the precise inter-proximal area involved in order to remove debris. These water pump type cleaners are therefore typically only of significant value in connection with teeth having braces thereupon which often trap large particles of food. It will be appreciated that if both debris and plaque are to be removed from teeth, at present a combination of a number of devices must be used, which is extremely time consuming and inconvenient.

In addition, in order for such practices and devices to be effective, a high level of consumer compliance with techniques and/or instructions is required. The user-to-user variation in time, cleaning/treating formula, technique, etc., will affect the cleaning of the teeth.

The present invention ameliorates one or more of the above mentioned disadvantages with existing oral hygiene apparatus and methods, or at least provides an alternative technology that is advantageous over known technology, and also may be used to ameliorate a detrimental condition or to improve cosmetic appearance of the oral cavity.

SUMMARY OF THE INVENTION

The invention is a device for directing a liquid onto a plurality of surfaces of the oral cavity of a mammal, the device including a handle, a neck and a head. The handle includes first and second ports located at the proximal end thereof for receiving the liquid from the liquid source, and first and second channels connected to the ports and running longitudinally through the handle for transporting the liquid through the handle to the neck of the device. The neck includes the first and second channels for transporting the liquid through the neck to the head. The head includes a cleaning component comprising a chamber for maintaining the liquid proximate the plurality of surfaces, where the internal space or volume of the chamber is defined and bounded by proximal and distal sealing membranes, first and second inner side walls extending longitudinally between the first and second sealing membranes, and a base inner wall extending horizontally between the first and second inner side walls and longitudinally between the proximal and distal sealing membranes. The inner side walls each include a plurality of openings through which liquid is directed onto the surfaces of the oral cavity. The device further includes a first manifold for containing a first portion of the liquid and providing the first portion to the chamber through the openings of the first inner side wall and a second manifold for containing a second portion of the liquid and providing the second portion to the chamber through the openings of the second inner side wall. The device further includes a first port for conveying the first portion of liquid to and from the first manifold, a second port for conveying the second portion of liquid to and from the second manifold; and means for providing an effective seal of the device within the oral cavity.

BRIEF DESCRIPTION OF THE DRAWINGS

FIG. 3b is an exploded view of the reciprocating flow controller of FIG. 3a;

FIG. 7 is a side view of the head portion of the embodiment of the device of FIG. 4;

FIG. 8 is a horizontal sectional view of FIG. 7;

FIG. 9 is a top view of the head portion of the embodiment of the device of FIG. 4;

FIG. 21 is a right side front perspective view of the neck and head of a fourth embodiment of an applicator device according to the present invention;

FIG. 22 is a right side front exploded view of the embodiment of the device of FIG. 21;

FIG. 23 is a left side bottom exploded view of the embodiment of the device of FIG. 21;

DETAILED DESCRIPTION OF THE INVENTION

Figure 1:
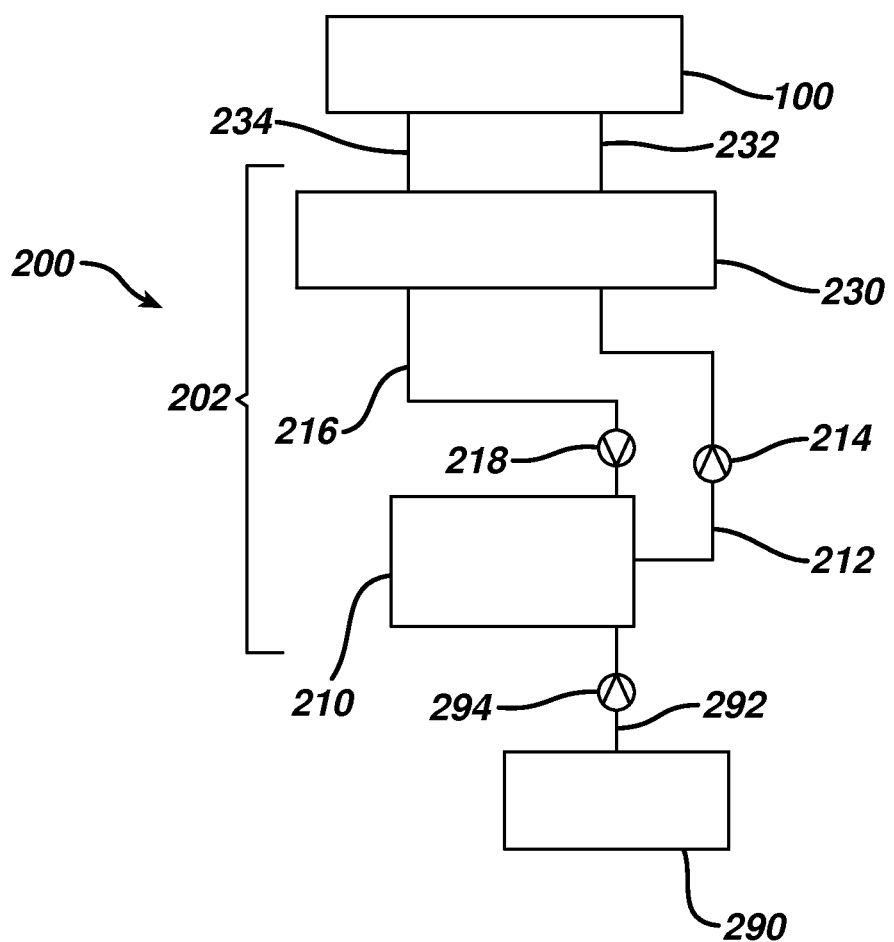
FIG. 1 is a schematic drawing of one embodiment of a system using a device according to the present invention.

The terms "fluid(s)" and "liquid(s)" are used interchangeably herein. As used herein, fluids or liquids may include gases or other particles and/or solids entrained therein.

The terms "reciprocating movement of liquid(s)" and "reciprocation of liquid(s)" are used interchangeably herein. As used herein, both terms mean alternating the direction of flow of the liquid(s) back and forth over surfaces of the oral cavity of a mammal from a first flow direction to a second flow direction that is opposite the first flow direction.

By "cleaning component", it is meant a component which cleans and/or treats teeth, gums and other oral tissue. By "cleaning fluid", it is meant a fluid which cleans and/or treats teeth, gums and other oral tissue.

By "effective fit or seal", it is meant that the level of sealing between the device for directing liquid onto and about the plurality of surfaces in the oral cavity is such that the amount of leakage of liquid from the device into the oral cavity during use is sufficiently low so as to reduce or minimize the amount of liquid used and to maintain comfort of the user, e.g. to avoid choking or gagging. Without intending to be limited, gagging is understood to be a reflex (i.e. not an intentional movement) muscular contraction of the back of the throat caused by stimulation of the back of the soft palate, the pharyngeal wall, the tonsillar area or base of tongue, meant to be a protective movement that prevents foreign objects from entering the pharynx and into the airway. There is variability in the gag reflex among individuals, e.g. what areas of the mouth stimulate it. In addition to the physical causes of gagging, there may be a psychological element to gagging, e.g. people who have a fear of choking may easily gag when something is placed in the mouth.

As used herein, "means for conveying liquid" includes structures through which liquid may travel or be transported throughout the systems and devices described herein and includes, without limitation passages, conduits, tubes, ports, portals, channels, lumens, pipes and manifolds. Such means for conveying liquids may be utilized in devices for providing reciprocation of liquids and devices for directing liquids onto and about surfaces of the oral cavity. Such conveying means also provides liquid to the device for directing liquids and provides liquid to the reciprocation means from a reservoir for containing liquid. The conveying means may also provide liquid from a base unit to a liquid reservoir contained within the device. Described herein are methods, devices and systems useful in providing a beneficial effect to an oral cavity of a mammal, e.g. a human.

Methods entail contacting a plurality of surfaces of the oral cavity with a liquid that is effective for providing the desired beneficial effect to the oral cavity. In such methods, reciprocation of the liquid(s) over the plurality of surfaces of the oral cavity may be provided under conditions effective to provide the desired beneficial effect to the oral cavity. Contact of the plurality of surfaces to be contacted by the liquid may be conducted substantially simultaneous. By substantially simultaneous, it is meant that, while not all of the plurality of surfaces of the oral cavity to be contacted are necessarily contacted by the fluid at the same time, the majority of the surfaces to be contacted are contacted simultaneously, or within a short period of time.

The conditions for providing the desired beneficial effect in the oral cavity may vary depending on the particular environment, circumstances and effect being sought. The different variables are interdependent in that they create a specific velocity of the liquid. The velocity requirement may be a function of the formulation in some embodiments. For example, with change in the viscosity, additives, e.g. abrasives, shear thinning agents, etc., and general flow properties of the formulation, velocity requirements of the jets may change to produce the same level of efficacy. Factors which may be considered in order to provide the appropriate conditions for achieving the particular beneficial effect sought include, without limitation, the velocity and/or flow rate and/or pressure of the liquid stream, pulsation of the liquid, the spray geometry or spray pattern of the liquid, the temperature of the liquid and the frequency of the reciprocating cycle of the liquid.

The liquid pressures, i.e. manifold pressure just prior to exit through the jets, may be from about 0.5 psi to about 30 psi, or from about 3 to about 15 psi, or about 5 psi. Flow rate of liquid may be from about 15 ml/s to about 25 ml/s. It should be noted that the larger and higher quantity of the jets, the greater flow rate required at a given pressure/velocity. Pulse frequency (linked to pulse length and delivery (ml/pulse), may be from about 0.5 Hz to about 50 Hz, or from about 5 Hz to about 25 Hz. Delivery pulse duty cycle may be from about 10% to 100%, or from about 40% to about 60%. It is noted that at 100% there is no pulse, but instead a continuous flow of liquid. Delivery pulse volume (total volume through all jets/nozzles) may be from about 0.2 ml to about 120 ml, or from about 0.5 ml to about 15 ml. Velocity of jetted pulse may be from about 4 cm/s to about 400 cm/s, or from about 20 cm/s to about 160 in/s. Vacuum duty cycle may be from about 10% to 100%, or from about 50% to 100%. It is noted that vacuum is always on. Volumetric delivery to vacuum ratio may be from about 2:1 to about 1:20, or from about 1:1 to 1:10. Once having the benefit of this disclosure, one skilled in the art will recognize that the various factors may be controlled and selected, depending on the particular circumstances and desired benefit sought.

The liquid(s) will include at least one ingredient, or agent, effective for providing the beneficial effect sought, in an amount effective to provide the beneficial effect when contacted with the surfaces of the oral cavity. For example, the liquid may include, without limitation, an ingredient selected from the group consisting of a cleaning agent, an antimicrobial agent, a mineralization agent, a desensitizing agent and a whitening agent. In certain embodiments, more than one liquid may be used in a single session. For example, a cleaning solution may be applied to the oral cavity, followed by a second solution containing, for example, a whitening agent or an antimicrobial agent. Solutions also may include a plurality of agents to accomplish more than one benefit with a single application. For example, the solution may include both a cleansing agent and an agent for ameliorating a detrimental condition, as further discussed below. In addition, a single solution may be effective to provide more than one beneficial effect to the oral cavity. For example, the solution may include a single agent that both cleans the oral cavity and acts as an antimicrobial, or that both cleans the oral cavity and whitens teeth.

Liquids useful for improving the cosmetic appearance of the oral cavity may include a whitening agent to whiten teeth in the cavity. Such whitening agents may include, without limitation, hydrogen peroxide and carbamide peroxide, or other agents capable of generating hydrogen peroxide when applied to the teeth. Such agents are well known within the art related to oral care whitening products such as rinses, toothpastes and whitening strips. Other whitening agents may include abrasives such as silica, sodium bicarbonate, alumina, apatites and bioglass.

It is noted that, while abrasives may serve to clean and/or whiten the teeth, certain of the abrasives also may serve to ameliorate hypersensitivity of the teeth caused by loss of enamel and exposure of the tubules in the teeth. For example, the particle size, e.g. diameter, of certain of the materials, e.g. bioglass, may be effective to block exposed tubules, thus reducing sensitivity of the teeth.

In some embodiments, the liquid may comprise an antimicrobial composition containing an alcohol having 3 to 6 carbon atoms. The liquid may be an antimicrobial mouthwash composition, particularly one having reduced ethanol content or being substantially free of ethanol, providing a high level of efficacy in the prevention of plaque, gum disease and bad breath. Noted alcohols having 3 to 6 carbon atoms are aliphatic alcohols. A particularly aliphatic alcohol having 3 carbons is 1-propanol.

In one embodiment the liquid may comprise an antimicrobial composition comprising (a) an antimicrobial effective amount of thymol and one or more other essential oils, (b) from about 0.01% to about 70.0% v/v, or about 0.1% to about 30% v/v, or about 0.1% to about 10% v/v, or about 0.2% to about 8% v/v, of an alcohol having 3 to 6 carbon atoms and (c) a vehicle. The alcohol may be 1-propanol. The liquid vehicle can be aqueous or non-aqueous, and may include thickening agents or gelling agents to provide the compositions with a particular consistency. Water and water/ethanol mixtures are the preferred vehicle.

Another embodiment of the liquid is an antimicrobial composition comprising (a) an antimicrobial effective amount of an antimicrobial agent, (b) from about 0.01% to about 70% v/v, or about 0.1% to about 30% v/v, or about 0.2% to about 8% v/v, of propanol and (c) a vehicle. The antimicrobial composition of this embodiment exhibits unexpectedly superior delivery system kinetics compared to prior art ethanolic systems. Exemplary antimicrobial agents which may be employed include, without limitation, essential oils, cetyl pyridium chloride (CPC), chlorhexidine, hexetidine, chitosan, triclosan, domiphen bromide, stannous fluoride, soluble pyrophosphates, metal oxides including but not limited to zinc oxide, peppermint oil, sage oil, sanguinaria, dicalcium dihydrate, aloe vera, polyols, protease, lipase, amylase, and metal salts including but not limited to zinc citrate, and the like. A particularly preferred aspect of this embodiment is directed to an antimicrobial oral composition, e.g. a mouthwash having about 30% v/v or less, or about 10% v/v or less, or about 3% v/v or less, of 1-propanol.

Yet another embodiment of the liquid is a reduced ethanol, antimicrobial mouthwash composition which comprises (a) an antimicrobial effective amount of thymol and one or more other essential oils; (b) from about 0.01 to about 30.0% v/v, or about 0.1% to about 10% v/v, or about 0.2% to about 8% v/v, of an alcohol having 3 to 6 carbon atoms; (c) ethanol in an amount of about 25% v/v or less; (d) at least one surfactant; and (e) water. Preferably the total concentration of ethanol and alcohol having 3 to 6 carbon atoms is no greater than 30% v/v, or no greater than 25% v/v, or no greater than 22% v/v.

In still another embodiment, the liquid is an ethanol-free antimicrobial mouthwash composition which comprises (a) an antimicrobial effective amount of thymol and one or more other essential oils; (b) from about 0.01% to about 30.0% v/v, or about 0.1% to about 10% v/v, or about 0.2% to about 8%, of an alcohol having 3 to 6 carbon atoms; (c) at least one surfactant; and (d) water.

The alcohol having 3 to 6 carbon atoms is preferably selected from the group consisting of 1-propanol, 2-propanol, 1-butanol, 2-butanol, tert-butanol and corresponding diols. 1-Propanol and 2-propanol are preferred, with 1-propanol being most preferred.

In addition to generally improving the oral hygiene of the oral cavity by cleaning, for example, removal or disruption of plaque build-up, food particles, biofilm, etc., the inventions are useful to ameliorate detrimental conditions within the oral cavity and to improve the cosmetic appearance of the oral cavity, for example whitening of the teeth. Detrimental conditions may include, without limitation, caries, gingivitis, inflammation, symptoms associated with periodontal disease, halitosis, sensitivity of the teeth and fungal infection. The liquids themselves may be in various forms, provided that they have the flow characteristics suitable for use in devices and methods of the present invention. For example, the liquids may be selected from the group consisting of solutions, emulsions and dispersions. In certain embodiments, the liquid may comprise a particulate, e.g. an abrasive, dispersed in a liquid phase, e.g. an aqueous phase. In such cases, the abrasive would be substantially homogeneously dispersed in the aqueous phase in order to be applied to the surfaces of the oral cavity. In other embodiments, an oil-in-water or water-in-oil emulsion may be used. In such cases, the liquid will comprise a discontinuous oil phase substantially homogeneously dispersed within a continuous aqueous phase, or a discontinuous aqueous phase substantially homogenously dispersed in a continuous oil phase, as the case may be. In still other embodiments, the liquid may be a solution whereby the agent is dissolved in a carrier, or where the carrier itself may be considered as the agent for providing the desired beneficial effect, e.g., an alcohol or alcohol/water mixture, usually having other agents dissolved therein.

Disclosed herein are devices, e.g. oral care devices, for example a dental cleaning apparatus, suitable for in-home use and adapted to direct liquid onto a plurality of surfaces of a tooth and/or the gingival area, as well as methods and systems utilizing such devices. In certain embodiments, the surfaces of the oral cavity to be contacted are contacted by the liquid substantially simultaneously. As used herein, reference to the gingival area includes, without limitation, reference to the sub-gingival pocket. The appropriate liquid may be directed onto a plurality of surfaces of teeth and/or gingival area substantially simultaneously in a reciprocating action under conditions effective to provide cleaning, and/or general improvement of the cosmetic appearance of the oral cavity and/or amelioration of a detrimental condition of the teeth and/or gingival area, thereby providing generally improved oral hygiene of teeth and/or gingival area. For example, one such device cleans teeth and/or the gingival area and removes plaque using an appropriate cleaning liquid by reciprocating the liquid back and forth over the front and back surfaces and inter-proximal areas of the teeth, thereby creating a cleaning cycle while minimizing the amount of cleaning liquid used.

Devices that provide reciprocation of the liquid comprise a means for controlling reciprocation of the liquid. The controlling means include means for conveying the liquid to and from the device for directing the liquid onto the plurality of surfaces of the oral cavity. In certain embodiments, the means for providing reciprocation of the liquid comprises a plurality of portals for receiving and discharging the liquid, a plurality of passages, or conduits, through which the liquid is conveyed, and means for changing the direction of flow of the liquid to provide reciprocation of the liquid, as described in more detail herein below. The controlling means may be controlled by a logic circuit and/or a mechanically controlled circuit.

In certain embodiments, devices for providing reciprocation may include a means for attaching or connecting the device to a reservoir for containing the liquid. The reservoir may be removably attached to the device. In this case, the reservoir and the device may comprise means for attaching one to the other. After completion of the process, the reservoir may be discarded and replaced with a different reservoir, or may be refilled and used again. In other embodiments, the reciprocating device will include a reservoir integral with the device. In embodiments where the device may be attached to a base unit, as described herein, the reservoir, whether integral with the device or removably attached to the device, may be refilled from a supply reservoir which forms a part of the base unit. Where a base unit is utilized, the device and the base unit will comprise means for attaching one to the other.

The device will comprise a power source for driving the means for reciprocating liquids. The power source may be contained within the device, e.g. in the handle of the device, for example, batteries, whether rechargeable or disposable. Where a base unit is employed, the base may include means for providing power to the device. In other embodiments, the base unit may include means for recharging the rechargeable batteries contained within the device.

The device may also include a timer for cleaning sections of the teeth, gums, or oral cavity. When the timer elapses, the device stops pumping as an indicator to move to the next section. The power is then reinitiated by the user. This may minimize the potential that the user move the device off of the area being cleaned and/or treated during device operation.

Means for providing reciprocation of liquids will include means for attaching the reciprocating means to a device for directing the liquid onto the plurality of surfaces of the oral cavity, e.g. a liquid applicator according to the invention. In certain embodiments, the applicator provides substantially simultaneous contact of the plurality of surfaces of the oral cavity by the liquid. The attachment means may provide removable attachment of the applicator to the device. The attachment means may be in the form of a quick disconnect structure. In such embodiments, multiple users may use their own applicator with a single reciprocating means. Devices for providing reciprocation as described above may be contained within a housing also containing other device components so as to provide a device suitable for providing liquid to the applicator, as described herein below.

Devices for directing liquid onto the plurality of surfaces of the oral cavity according to the present invention, e.g. the liquid applicator, comprise a handle, a neck, and a head. It is noted that terms device for directing liquid, liquid applicator and liquid application device are used interchangeably herein.

The handle of the liquid applicator includes first and second ports located at a proximal end of the handle for receiving the liquid from the source, whether it be from a base reservoir unit, or the reciprocation means. The ports may interface with the liquid source via, for example, hoses, conduits or other appropriate means for conveying the liquid from the liquid source to the fluid applicator. The handle also includes first and second channels for transporting the liquid through the handle and to the neck and head portions of the liquid applicator. The first and second channels are connected to the first and second ports, respectively, at the proximal end of the handle and extend longitudinally through the handle to the neck of the applicator.

The neck of the liquid applicator includes the first and second channels for transporting the fluid disposed within and extending longitudinally there through to the head of the liquid applicator. The channels then terminate in a manifold feed connecting the fluid channels with respective fluid manifold located in the head of the applicator.

The head includes a cleaning component that comprises a chamber for maintaining the liquid proximate the plurality of surfaces, i.e. liquid-contacting-chamber (LCC). By "proximate", it is meant that the liquid is maintained in contact with the surfaces. The LCC is defined by the space bounded by proximal and distal sealing membranes, first and second inner side walls extending longitudinally between the first and second sealing membranes, and a base inner wall extending horizontally between the base of the first and second inner side walls and longitudinally between the proximal and distal sealing membranes. The first and second inner side walls of the cleaning component each include a plurality of openings, or slots, through which the liquid is directed to contact the plurality of surfaces of the oral cavity.

The head of the liquid applicator also includes a first manifold for containing a first portion of liquid and providing same to the LCC through the openings of the first inner side wall, a second manifold for containing a second portion of liquid and providing same to the LCC through the openings of the second inner side wall, a first port for conveying the first portion of liquid to and from the first manifold, and a second port for conveying the second portion of liquid to and from the second manifold.

The cleaning component design may be optimized for maximum effectiveness as it relates to the size, shape, thickness, materials, volume created around the teeth/gingiva, nozzle design and placement as it relates to the oral cavity and the teeth in conjunction with the manifold and gingival margin seal to provide comfort and minimize the gagging reflex of the user. The combination of the above provides effective contact of the teeth and gingival area by the liquid.

The cleaning component provides a controlled and isolated environment with known volume, i.e. the LCC, to contact teeth and/or gingival area with liquids, and then to remove spent liquids, as well as debris, plaque, etc., from the LCC without exposing the whole oral cavity to liquid, debris, etc. This decreases the potential for ingestion of the liquids. The cleaning component also allows increased flow rates and pressure of liquids without drowning the individual nozzles when significant flow rates are required to provide adequate cleaning, for example. The cleaning component also allows reduced liquid quantities and flow rates when required, as only the area within the LCC is being contacted with liquid, not the entire oral cavity. The cleaning component also allows controlled delivery and duration of contact of liquid on, through and around teeth and the gingival area, allowing increased concentrations of liquids on the area being contacted by the liquid, thereby providing more effective control and delivery of liquid.

The number and location of openings, also referred to herein as slots, jets or nozzles, contained within the inner walls of the cleaning component through which the liquid is directed will vary and be determined based upon the circumstances and environment of use, the particular user and the beneficial effect being sought. The cross-sectional geometry of the openings may be circular, elliptical, trapezoidal, or any other geometry that provides effective contact of the surfaces of the oral cavity by the liquid. The location and number of openings may be designed to direct jets of liquid in a variety of spray patterns effective for providing the desired beneficial effect. Opening diameters may be from about 0.1 to about 3 mm, or from about 0.2 mm to about 0.8 mm, or about 0.5 mm, to provide effective cleaning and average jet velocities and coverage.

Optimal opening placement and direction/angles allows coverage of substantially all teeth surfaces in the area of the oral cavity to be contacted by liquid, including but not limited to interdental, top, side, back, and gingival pocket surfaces. In alternate embodiments, the openings could be of different sizes and different shapes to provide different cleaning, coverage and spray patterns, to adjust velocities, density and fan patterns (full cone, fan, partial, cone, jet), or due to formulation consideration. The cleaning component may be an elastomeric material such as ethylene vinyl acetate (EVA), thermoplastic elastomer (TPE), or silicone, to allow motion of the inner walls and provide a greater jet coverage area with minimal mechanics, reducing the volumetric flow requirements to achieve optimized performance, while providing a softer and more flexible material to protect the teeth and/or gingiva if direct contact with the teeth and/or gingiva is made. A flexible membrane may also provide acceptable fitment over a large range of users, due to its ability to conform to the teeth and/or gingiva, and act as a flexible gum-sealing membrane to provide an effective seal. Alternatively, the cleaning component could be made of a rigid or semi-rigid material, such as but not limited to a thermoplastic.

In an alternate embodiment, the cleaning component could also include abrasive elements such as filaments, textures, polishing elements, additives (silica, etc.), and other geometric elements that could be used for other cleaning and/or treatment requirements as well as ensuring minimal distance between the teeth and cleaning component for, but not limited to, treatment, cleaning, and positioning. The cleaning component could be created via a variety of methods such as, but not limited to, machining, injection molding, blow molding, extrusion, compression molding, and/or vacuum forming.

The material for the manifold would be a semi-rigid thermoplastic, which would provide the rigidity necessary not to collapse or burst during the controlled flow of the liquids, but to provide some flexibility when fitting within the user's mouth for cleaning component insertion, sealing/position and removal. To minimize fabrication complexity, number of components and tooling cost, the dual manifold is created when assembled with the LCCM. The manifold could also be multi-component to provide a softer external "feel" to the teeth/gums utilizing a lower durometer elastomeric material, such as, but not limited to, a compatible thermoplastic elastomer (TPE). The manifold could be created via a variety of methods such as, but not limited to machining, injection molding, blow molding, compression molding, or vacuum forming.

Devices of the invention also comprise a first port for conveying the liquid to and/or from the first manifold and a second port for conveying the liquid to and from the second manifold, and means for providing an effective seal of the directing means within the oral cavity, i.e. a gingival and/or teeth seal. In certain embodiments, the first and second ports may serve both to convey liquid to and from the first and second manifolds and to attach the applicator to the means for providing liquid to the applicator. In other embodiments, the directing means may further include means for attaching the directing means to means for providing liquid to the directing means.

FIG. 1 is a schematic drawing of an embodiment of a system utilizing devices according to the present invention. The figure shows system 200, with components including: means for providing reciprocation 202 of liquid in the oral cavity, means for directing the liquid onto the plurality of surfaces of the oral cavity, in this instance shown as liquid applicator 100, and liquid supply reservoir 290. Means for providing reciprocation 202 of liquids may include, in this embodiment, delivery/collection device 210, reciprocating flow controller 230, tubes 212, 216, and 292 for conveying the liquid throughout the system, and liquid one-way flow valves 214, 218 and 294. Tubes 232 and 234 provide for conveyance of the liquid from reciprocating flow controller 230 to liquid applicator 100.

In some embodiments, delivery/collection device 210 may be a piston pump. Liquid supply reservoir 290 may be made of glass, plastic or metal. Liquid supply reservoir 290 may be integral to system 200 and refillable. In some embodiments, liquid supply reservoir 290 may be a replaceable liquid supply, such as a single or multi-use cartridge, detachably connected to system 200.

In some embodiments, liquid supply reservoir 290 and/or tubes 212, 292, may include a heat source to pre-warm the liquid prior to direction into applicator 100 for application to the surfaces of the oral cavity. The temperature should be maintained within a range effective to provide efficacy and comfort to the user during use.

Applicator 100, discussed in detail herein below, may be detachably connected to reciprocating means 202 by way of tubes 232, 234 and further attachment means (not shown). It could be one or two sided with internally, easily cleanable filters for trapping food particles. When positioned within the oral cavity, e.g. about the teeth and gums, applicator 100 forms an effective fit or seal against the gums and directs liquid against surfaces of the oral cavity, e.g. surfaces of the teeth.

Liquid in liquid supply reservoir 290 flows through tube 292 to delivery/collection device 210. Liquid flow through tube 292 is controlled by one-way flow valve 294. From delivery/collection device 210, liquid flows through tube 212 to reciprocating flow controller 230. One-way flow valve 214 controls the liquid flow through tube 212. Liquid flows from reciprocating flow controller 230 to applicator 100 either through tube 232 or 234, depending on the flow direction setting of reciprocating flow controller 230. Liquid flows from applicator 100, through either tube 234 or 232 back to reciprocating flow controller 230, and from reciprocating flow controller 230 to delivery/collection device 210, through tube 216. One-way flow valve 218 controls the liquid flow through tube 216.

The actions of delivery/collection device 210 may be controlled by a logic circuit, which may include a program to start the reciprocation cycle, a program to execute the reciprocation cycle, i.e. to cause liquid to be reciprocated about the teeth, thereby providing the beneficial effect to the oral cavity, e.g. cleaning the teeth, a program to empty applicator 100 at the end of the reciprocation cycle, and a self-cleaning cycle to clean the system between uses, or at pre-set or automatic cleaning times.

Though not shown, a face panel with a series of switches and indicator lights may also be incorporated into system 200. Switches may include, but are not limited to, on/off, fill applicator 100, run the reciprocation program, empty system 200, and clean system 200. Indicator, or display, lights include, but are not limited to, power on, charging, reciprocation program running, system emptying, cleaning results or feedback, and self-cleaning cycle in operation. In embodiments where liquid is pre-warmed prior to direction into applicator 100, a display light could be used to indicate that the liquid is at the proper temperature for use.

One method of using system 200 to clean teeth is as follows. In the first step, the user positions applicator 100 in the oral cavity about the teeth and gingival area to be cleaned. Delivery/collection device 210 is activated to begin drawing cleaning liquid from liquid supply reservoir 290 through tube 292 and one-way flow valve 294. Once delivery/collection device 210 is sufficiently filled, delivery/collection device 210 is activated to begin dispensing cleaning liquid to applicator 100 via tube 212, one-way flow valve 214, reciprocating flow controller 230, and tube 232. Cleaning liquid will be prevented from flowing through tubes 216 and 292 by one-way flow valves 218 and 294, respectively. Delivery/collection device 210 is activated to begin drawing cleaning liquid from applicator 100 through tube 234, then through reciprocation flow controller 230, then through tube 216 and one-way flow valve 218. Cleaning liquid will be prevented from flowing through tube 212 by one-way flow valve 214. If there is insufficient cleaning liquid to adequately fill delivery/collection device 210, additional cleaning liquid may be drawn from liquid supply reservoir 290 through tube 292 and one-way flow valve 294. The direction of the liquid flow is then reversed. To reciprocate the cleaning liquid, steps 2 and 3 are repeated after the flow direction is reversed, cycling cleaning liquid between delivery/collection device 210 and applicator 100, using tubes 234 and 232, respectively. The reciprocation cycle described continues until the time required for cleaning has expired, or the desired numbers of cycles are complete. It is noted that there may be a delay between the delivery of the fluid to applicator 100 and the drawing of the fluid from applicator 100 (in either or both, directions), allowing a dwell time where the liquid is allowed to contact the teeth without flow.

Figure 2:
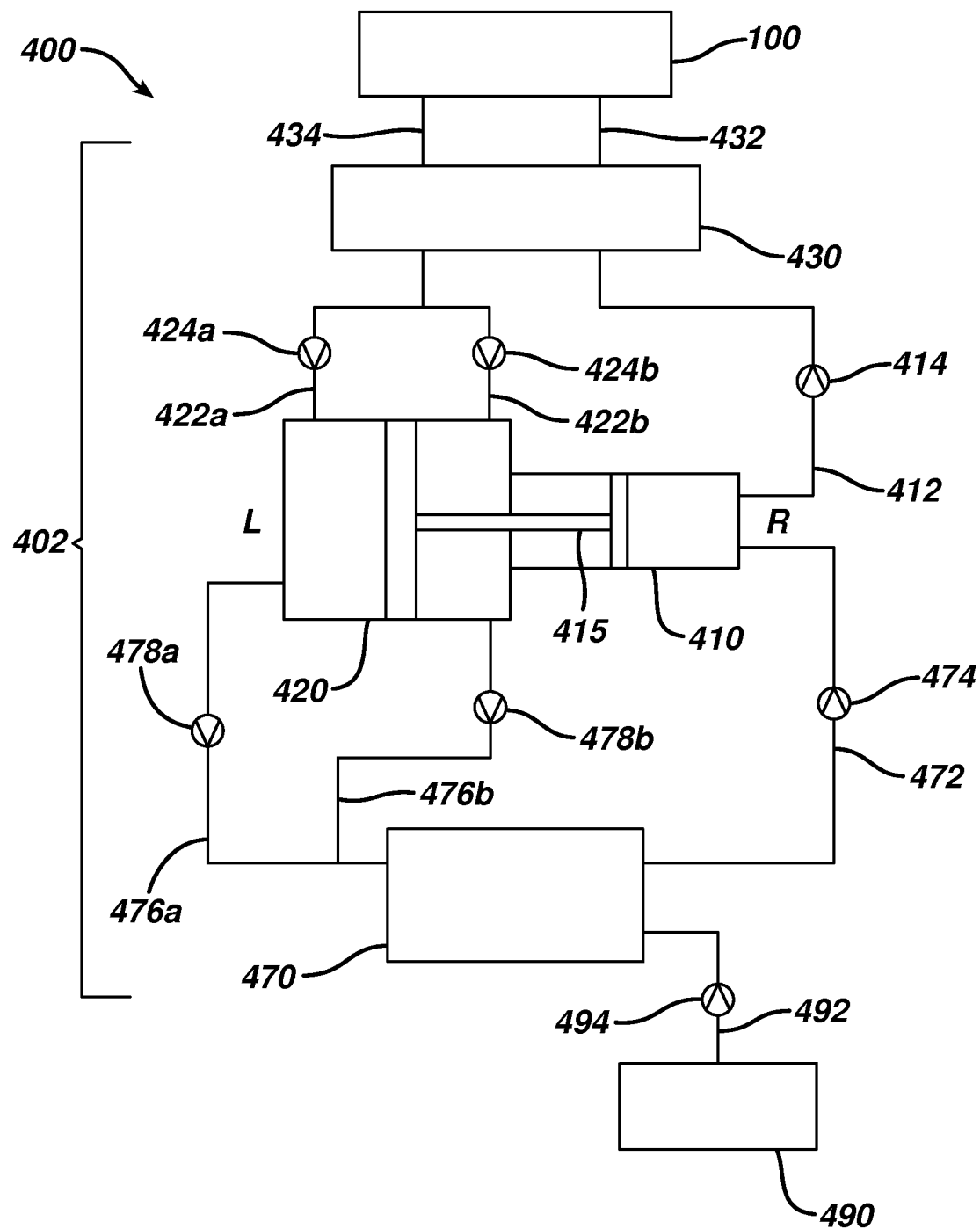
FIG. 2 is a schematic drawing of an alternative embodiment of a system using a device according to the present invention.

FIG. 2 is a schematic drawing of an alternative embodiment of a system utilizing devices according to the present invention. The figure shows system 400, with components including: means for providing reciprocation 402 of liquids in the oral cavity, liquid reservoir 470, liquid supply reservoir 490, and means for directing the liquid onto the plurality of surfaces of the oral cavity, in this instance shown as liquid applicator 100. Means for providing reciprocation 402 may include delivery device 410, collection device 420, reciprocating flow controller 430, tubes 412, 422a, 422b, 472, 476, and 492, and solution one-way flow valves 414, 424a, 424b, 474, 478, and 494. Tubes 432 and 434 provide for conveyance of the liquid from reciprocating flow controller 430 to liquid applicator 100.

In the present embodiment, delivery device 410 and collection device 420 are housed together as a duel action piston pump, with common piston 415. Liquid supply reservoir 490 and liquid reservoir 470 may be made of glass, plastic, or metal. Liquid supply reservoir 490 may be integral to system 400 and refillable. In some embodiments, liquid supply reservoir 490 may be a replaceable liquid supply, detachably connected to system 400.

In some embodiments, any of liquid supply reservoir 490, liquid reservoir 470, or tubes 412, 472, 492, may include a heat source to pre-warm cleaning solution prior to direction into applicator 100 for application to the teeth. The temperature should be maintained within a range effective to provide comfort to the user during use.

Applicator 100 may be detachably connected to reciprocating means 402 by way of tubes 432, 434 and other attachment means (not shown).

Liquid in liquid supply reservoir 490 flows through tube 492 to liquid reservoir 470. Liquid in reservoir 470 flows through tube 472 to delivery device 410. Liquid flow through tube 472 is controlled by one-way flow valve 474. From delivery device 410, liquid flows through tube 412 to reciprocating flow controller 430. One-way flow valve 414 controls the liquid flow through tube 412. Liquid flows from reciprocating flow controller 430 to liquid applicator 100 through tube 432 or tube 434, depending on the flow direction. Liquid flows from liquid applicator 100, through tube 434 or tube 432, again depending on the flow direction, back to reciprocating flow controller 430, and from reciprocating flow controller 430 to collection device 420, through tubes 422a and 422b. One-way flow valves 424a and 424b control the liquid flow through the tubes. Finally, liquid flows from collection device 420 to liquid reservoir 470 through tubes 476a and 476b. One-way flow valves 478a and 478b control the liquid flow through the tubes.

The actions of delivery device 410 and collection device 420 may be controlled by a logic circuit, which may include a program to the start reciprocation cycle, a program to execute the reciprocation cycle, i.e. to cause solution to be reciprocated about the plurality of the surfaces of the oral cavity, thereby providing the beneficial effect, a program to empty liquid applicator 100 at the end of the cycle, and a self-cleaning cycle to clean the system between uses, or at pre-set or automatic cleaning times.

One method of using system 400 to clean teeth is as follows. Prior to use, cleaning liquid in liquid supply reservoir 490 flows through tube 492 and one-way valve 494 to cleaning liquid reservoir 470. In some embodiments, liquid supply reservoir 490 is now disconnected from system 400.

In the first step, the user positions liquid applicator 100 in the oral cavity about the teeth and oral cavity to be contacted. The cleaning process is as follows:

Piston 415 is activated to begin drawing cleaning liquid to delivery device 410 from cleaning liquid reservoir 470 through tube 472 and one-way flow valve 474. To accomplish this, piston 415 translates from right to left ("R" to "L" on FIG. 3). Once delivery device 410 is sufficiently filled, delivery device 410 is activated to begin dispensing cleaning liquid to applicator 100 via tube 412, one-way flow valve 414, reciprocating flow controller 430, and tube 432. To accomplish this, piston 415 translates from left to right ("L" to "R" on FIG. 3). The "L" to "R" motion of piston 415 causes collection device 420 to begin drawing cleaning liquid from applicator 100 via tube 434, reciprocating flow controller 430, tube 422a, and one-way flow valve 424a. Cleaning liquid will be prevented from flowing through tubes 472 and 422a, by one-way flow valves 474 and 424b. Any excess cleaning liquid in collection device 420 will begin dispensing to cleaning liquid reservoir 470 via tube 476b and one-way valve 478b. Cleaning liquid will be prevented from flowing through tube 422b by one-way flow valve 424b. To cycle cleaning solution, the delivery steps are repeated, cycling cleaning liquid between cleaning solution reservoir 470 and liquid applicator 100. The process continues to run until the time required for cleaning has expired, or the desired numbers of cycles are complete.

Figure 3A:
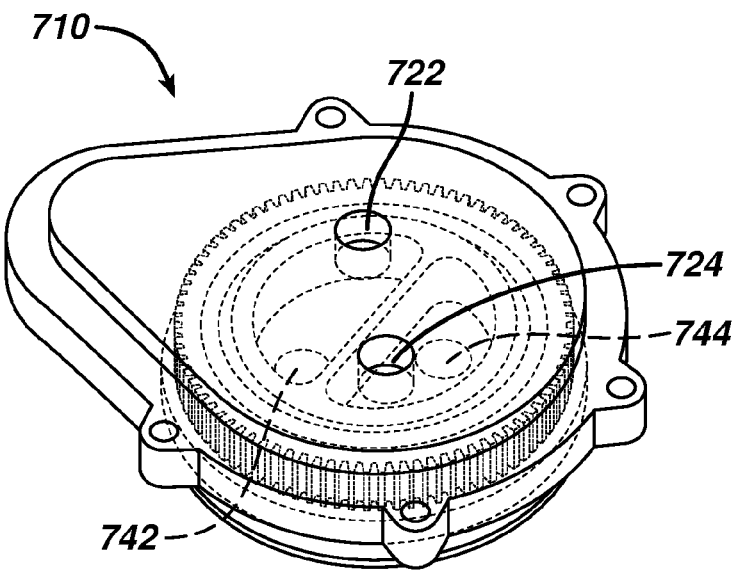
FIG. 3a is a perspective drawing of an embodiment of a reciprocating flow controller.
Figure 3B:
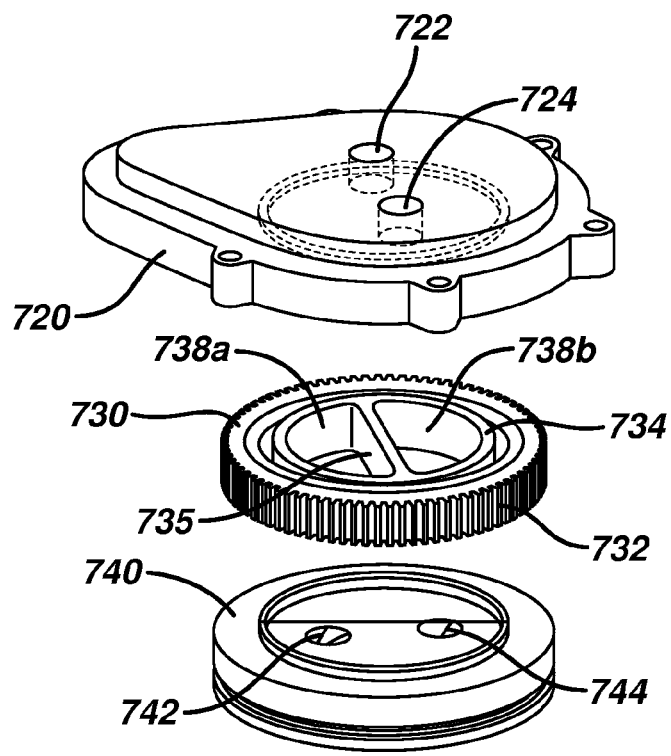

Each embodiment described in FIGS. 1 and 2 includes optional reciprocating flow controller (230, 430 in FIG. 1, FIG. 2, respectively). A perspective drawing and an exploded view of an embodiment of a reciprocating flow controller according to the present invention is shown in FIG. 3a and FIG. 3b, respectively. The figures show reciprocating flow controller 710 with cap 720, flow diverter disk 730, and base 740. Cap 720 has cap ports 722 and 724. Base 740 has base ports 742 and 744. Flow diverter disk 730 is disposed between cap 720 and base 740, and has panel 735 for diverting liquid flow, and position adjuster 732 in the form of a gear.

Figure 3C:
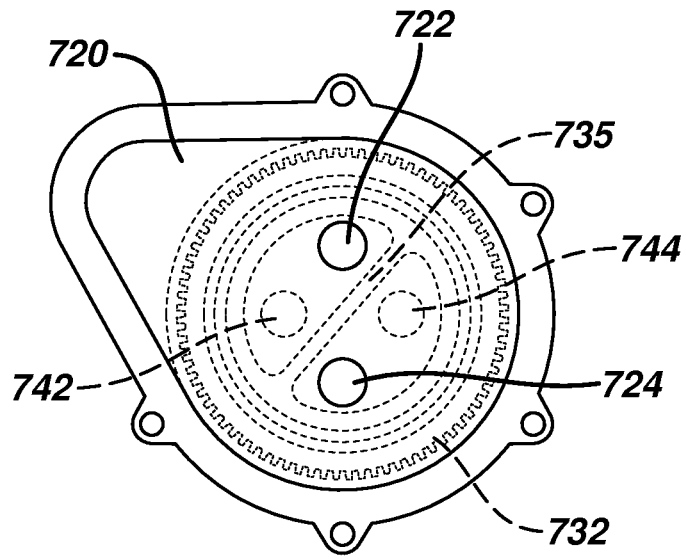
FIG. 3c is a top view of the reciprocating flow controller of FIG. 3a in its first position.

FIG. 3c is a top view of reciprocating flow controller 710 in its first position. In this position, incoming liquid, such as liquid in tube 212 of FIG. 1, enters reciprocating flow controller 710 through base port 742. The liquid exits reciprocating flow controller 710 through cap port 722, such as liquid in tube 232 of FIG. 1. Returning liquid, such as liquid in tube 234 of FIG. 1, reenters reciprocating flow controller 710 through cap port 724. The liquid re-exits reciprocating flow controller 710 through base port 744, such as liquid in tube 216 of FIG. 1.

Figure 3D:
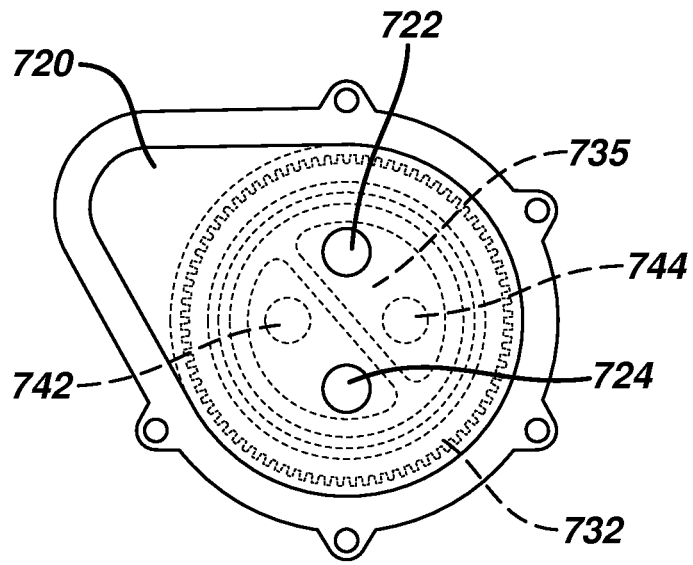
FIG. 3d is a top view of the reciprocating flow controller of FIG. 3a in its second position.

FIG. 3d is a top view of the reciprocating flow controller 710 in its second position. In this position, incoming liquid, such as liquid in tube 212 of FIG. 1, enters reciprocating flow controller 710 through base port 742. The liquid exits reciprocating flow controller 710 through cap port 724 such as liquid in tube 234 of FIG. 1. Returning liquid, such as liquid in tube 232 of FIG. 1, reenters reciprocating flow controller 710 through cap port 722. The liquid exits reciprocating flow controller 710 through base port 744, such as liquid in tube 216 of FIG. 1.

Reciprocation of liquid in liquid applicator 100 of FIG. 1 is achieved by switching reciprocating flow controller 710 between its first and second positions. It has been found that the width of panel 735 relative to the diameters of cap ports 722 and 724 and base ports 742 and 744 is critical to the performance of reciprocating flow controller 710. If the width of panel 735 is equal to or greater than any of the diameters, then one or more of cap ports 722 and 724 or base ports 742 and 744 may be blocked, or isolated, during part of the reciprocation, resulting in suboptimal performance or device failure. A channel may be located in panel 735 to avoid this condition.

The oral hygiene system may be comprised of several components including, but not limited to, a base station, a unit for containing means for providing reciprocation of liquid about the plurality of surfaces within the oral cavity, and the device for directing the liquid onto the plurality of surfaces of the oral cavity to be treated/cleaned, i.e. the liquid applicator.

The system is suitable for in-home use and adapted to direct liquid onto a plurality of surfaces of a tooth. The device cleans teeth and removes plaque using a cleaning solution that may be reciprocated back and forth, creating a cleaning cycle and minimizing cleaning solution used. The base station may charge a rechargeable battery, hold liquid reservoirs, house diagnostic components, provide feedback to the user, and potentially clean the applicator.

The means for providing reciprocation will have a powered pump that will deliver liquid from the reservoir to the liquid applicator. The direction of flow may be reciprocated with liquid control valving, by a specialized pump (reversing its direction, etc), reversible check valves, or other similar means. The cycle time and flow velocity for each stage of the cycle will be variable and in some embodiments, be customized to each individual user.

Figure 4:
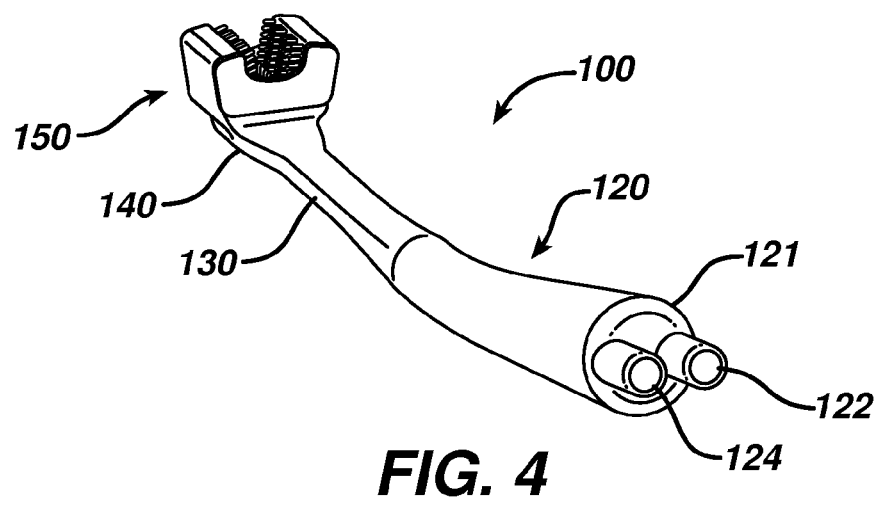
FIG. 4 is a right side front perspective view of a first embodiment of an applicator device according to the present invention.
Figure 5:
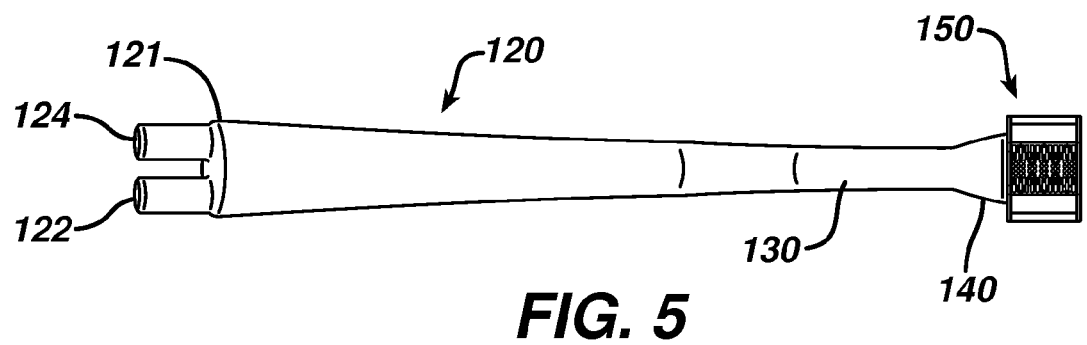
FIG. 5 is a top view of the embodiment of the device of FIG. 4.
Figure 6:
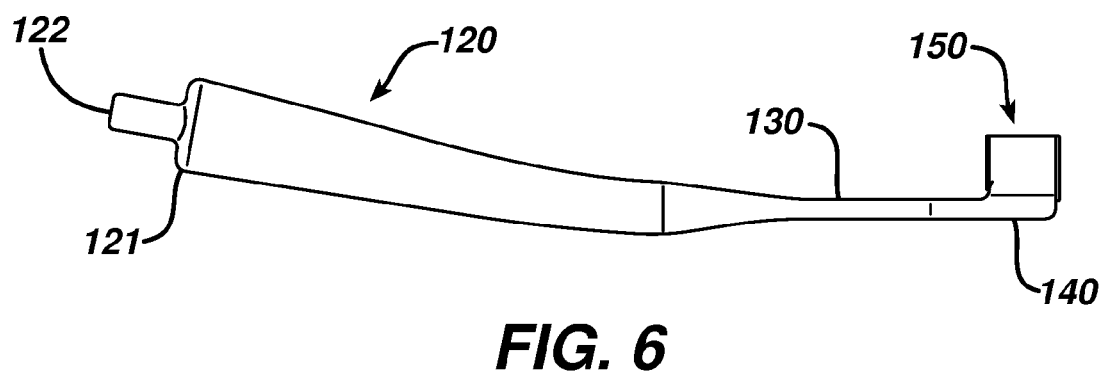
FIG. 6 is a side view of the embodiment of the device of FIG. 4.

The third major component of the apparatus is the device for directing liquid to the plurality of surfaces in the oral cavity to be cleaned/treated, i.e. the liquid applicator. FIGS. 4 to 11 show a first embodiment of a liquid application device. FIG. 4 is a right side front perspective view of a first embodiment of liquid applicator device 100 according to the present invention. FIG. 5 is a top view of liquid applicator 100 of FIG. 4, while FIG. 6 is a side view of liquid applicator 100 of FIG. 4. The figures show applicator 100 with handle 120, neck 130, and head 140. First port 122 and second port 124 for receiving liquid from the liquid reservoir are located at proximal end 121 of handle 120, and connect to first and second channels (not shown) originating at proximal end 121. Cleaning component 150 is disposed on the facing of head 140.

FIG. 7 is a side view of neck 130 and head 140 of liquid applicator 100 of FIG. 4. The figure shows cleaning component 150 disposed on the facing of head 140. Proximal sealing membrane 152 and distal sealing membrane 154 are located at the ends of cleaning component 150. FIG. 8 is a horizontal sectional view of FIG. 7 along the 8-8 plane. The figure shows first fluid channel 142 and second fluid channel 144 disposed in neck 130 and head 140. First fluid channel 142 terminates in first manifold feed 146, which connects first fluid channel 142 to a first fluid manifold (not shown) in cleaning component 150. Second fluid channel 144 terminates in second manifold feed 148, which connects second fluid channel 144 to a second fluid manifold (not shown) in cleaning component 150.

Figure 10:
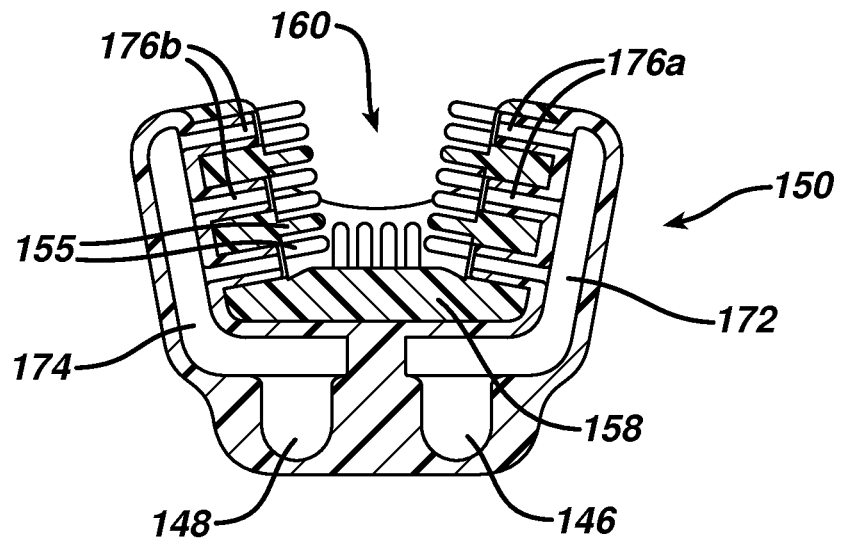
FIG. 10 is a vertical sectional view of FIG. 9 along the 10-10 plane.
Figure 11:
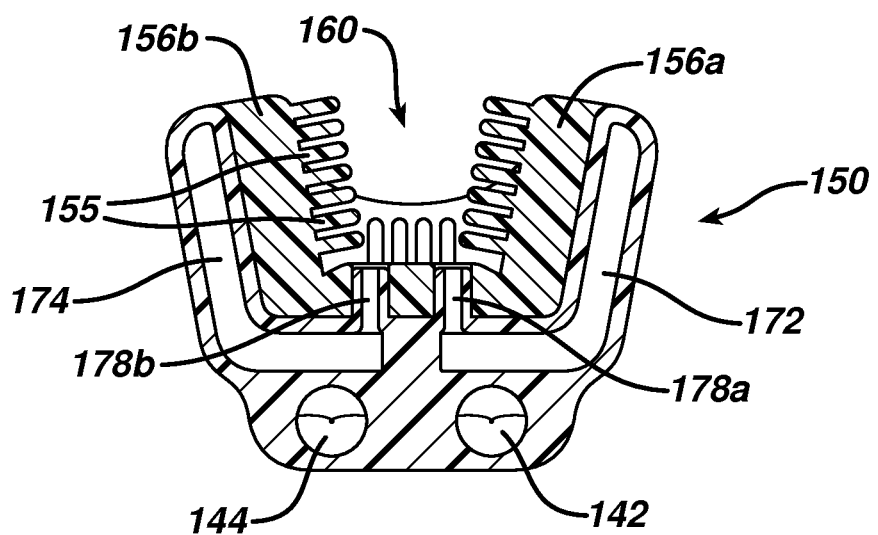
FIG. 11 is a vertical sectional view of FIG. 9 along the 11-11 plane.

FIG. 9 through 11 are views of cleaning component 150. FIG. 9 is a top view of cleaning component 150, including proximal sealing membrane 152, distal sealing membrane 154, cleaning elements 155, first side wall 156a, second side wall 156b, and base inner wall 158. Though the figures show cleaning elements 155 located on first side wall 156a, second side wall 156b, and base inner wall 158, cleaning elements 155 may be located on only one side wall (156a or 156b) or on only base inner wall 158, or on any combination in other embodiments. In addition, the shape, size, number and layout of cleaning elements 155 may be optimized for improved cleaning.

FIG. 10 is a vertical sectional view of FIG. 9 along the 10-10 plane, and FIG. 11 is a vertical sectional view of FIG. 9 along the 11-11 plane. The figures show first manifold feed 146 connected to first fluid manifold 172, and second manifold feed 148 connected to second fluid manifold 174. First fluid manifold 172 features first side nozzles 176a, which pass through first side wall 156a, and first bottom nozzles 178a, which pass through base inner wall 158. Second fluid manifold 174 features second side nozzles 176b, which pass through second side wall 156b, and second bottom nozzles 178b, which pass through base inner wall 158. The liquid-contacting chamber (LCC) 160 is defined by first side wall 156a, second side wall 156b, proximal sealing membrane 152, distal sealing membrane 154, and base inner wall 158.

It is to be understood that the configuration of first side nozzles 176a, second side nozzles 176b, first bottom nozzles 178a, and second bottom nozzles 178b in FIGS. 4 to 11 are only one embodiment of nozzle configuration. The configuration of the nozzles, as well as the geometry of the nozzle openings, may change.

The proximal sealing membrane 152 and distal sealing membrane 154 provide a flexible and universal sealing mechanism to minimize leakage into the oral cavity while redirecting flow onto and around teeth, to maximize treatment/cleaning area to get to hard-to-reach-places (HTRP). The membrane can provide an elastic function across the lumen longitudinal axis to form around the teeth and gums.

Base inner wall 158 provides the flexibility required for effective fit or sealing within the oral cavity and allowing redirection and flow of fluids back towards the teeth and/or gingival surfaces. Base inner wall 158 may be a flexible membrane for providing an effective seal.

In one embodiment of an operation, liquid enters first fluid channel 142 through first port 122 by pressure and then passes through first fluid manifold 172 and enters LCC 160 through first side nozzles 176a and first bottom nozzles 178a. A vacuum is pulled on second port 124 to pull the liquid through second side nozzles 176b and second bottom nozzles 178b, into second fluid manifold 174, through second fluid channel 144 and finally into second port 124. In this embodiment, jets of liquid are first directed from the first manifold onto the first surfaces of the teeth and/or gingival area from one side of the LCC 160, directed through, between, and around the surfaces of the teeth and/or gingival area from the other side of LCC 160 and into the second manifold to provide controlled interdental, gumline, surface and/or gingival area cleaning or treatment. Next, the flow in the manifolds is reversed. Cleaning liquid enters second fluid channel 144 through second port 124 by pressure and then passes through second fluid manifold 174 and enters LCC 160 through second side nozzles 176b and second bottom nozzles 178b. A vacuum is pulled on first port 122 to pull the liquid through first side nozzles 176a and first bottom nozzles 178a, into first fluid manifold 172, through first fluid channel 142 and finally into first port 122. In the second portion of this embodiment, jets of liquid are directed from the second manifold onto the second surfaces of the teeth and/or gingival area, and directed through, between, and around the surfaces of the teeth and/or gingival area. The alternating of pressure/vacuum through a number of cycles creates a turbulent, repeatable and reversible flow to provide reciprocation of liquid about the plurality of surfaces of the oral cavity to substantially simultaneously contact the surfaces of the oral cavity with liquid, thereby providing the desired beneficial effect.

In another embodiment, it may be preferable to deliver the liquid through one or both manifolds simultaneously, flooding LCC 160, submerging the teeth and gums for a period of time and then evacuating LCC 160 after a set period of time through one or both manifolds. Here, cleaning or treating liquid simultaneously enters first port 122 and second port 124, simultaneously passes through first fluid channel 142, second fluid channel 144, first manifold feed 146, second manifold feed 148, first fluid manifold 172, and second fluid manifold 174 by pressure and then enters LCC 160 simultaneously through first side nozzles 176a, second side nozzles 176b, first bottom nozzles 178a, and second bottom nozzles 178b. To evacuate LCC 160, a vacuum is simultaneously pulled through first port 122 and second port 124. Cleaning or treatment liquid is pulled through first side nozzles 176a and first bottom nozzles 178a, into first fluid manifold 172, and through second side nozzles 176b and second bottom nozzles 178b, into second fluid manifold 174.

It is also possible to deliver different liquid compositions to first fluid manifold 172 and second fluid manifold 174. The different liquid compositions could then combine in LCC 160 for improved cleaning efficacy or treatment effects.

Figure 12:
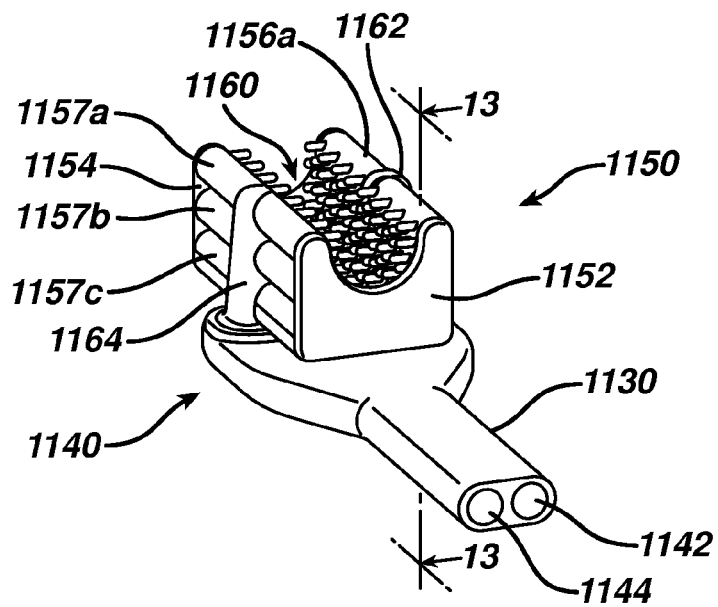
FIG. 12 is a right side front perspective view of a second embodiment of the neck and head of an applicator device according to the present invention.
Figure 13:
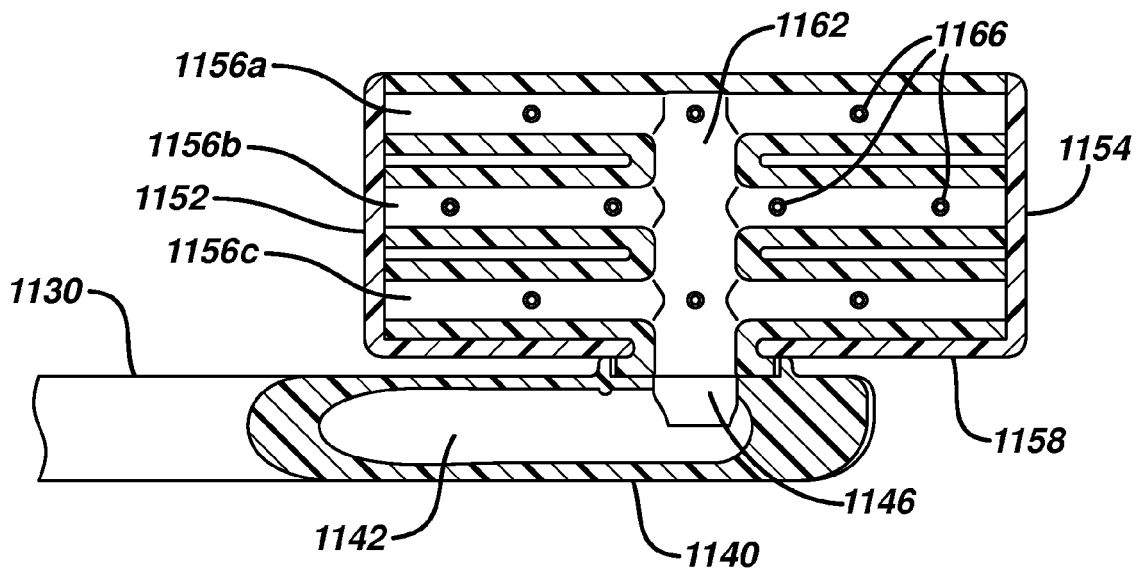
FIG. 13 is a vertical sectional view of FIG. 12 along the 13-13 plane.

Although the embodiment of FIGS. 4 through 11 show a single cleaning component 150 on head 140, it is to be understood that a second cleaning component that is similar to cleaning component 150 may disposed on the opposite facing of head 140. The second cleaning component would provide substantially simultaneous contact of a plurality of surfaces of both top and bottom sections of the oral cavity FIGS. 12 and 13 show a second embodiment of a liquid application device of the present invention. FIG. 12 is a top, rear perspective view of neck 1130 and head 1140 of a liquid application device according to the present invention. The figure shows first fluid channel 1142 and second fluid channel 1144 disposed in neck 1130. Cleaning component 1150 is disposed on the facing of head 1140.

FIG. 13 is a vertical sectional view of FIG. 12 along the 13-13 plane. The figures show first fluid channel 1142 connected to first manifold feed 1146, which is connected to first fluid manifold 1162 in cleaning component 1150. First manifold feed 1146 feeds first liquid lumens 1156a, 1156b, 1156c. The figures also show first nozzles 1166 in first liquid lumens 1156a, 1156b, 1156c. Though not shown in the figures, second fluid channel 1144 connected to second manifold feed 1148, which is connected to second fluid manifold 1164 in cleaning component 1150. Second manifold feed 1148 feeds second liquid lumens 1157a, 1157b, 1157c and second nozzles 1168 in first liquid lumens 1157a, 1157b, 1157c.

It is to be understood that the layout of first nozzles 1166 and second nozzles 1168 are only one embodiment of nozzle configuration. The layout of the nozzles, as well as the geometry of the nozzle openings may change.

FIGS. 12 and 13 show cleaning component 1150 with six liquid lumens (1156a, 1156b, 1156c, 1157a, 1157b, and 1157c). In others embodiments, cleaning component 1150 may be formed with two, three, four, five, seven, eight, nine, ten, or even more liquid lumens.

The multi-lumen design provides bidirectional or dedicated lumens for flow and vacuum that are self-reinforcing and therefore do not collapse under vacuum or rupture under pressure while in use, maximizing the structural integrity, while minimizing the size of the overall cleaning component 1150 for user comfort during insertion, in-use, and upon removal. This decreased size also serves to provide an enhanced effective seal of the applicator in the oral cavity.

The multiple lumens (1156a, 1156b, 1156c, 1157a, 1157b, 1157c) as connected above form a lumen hinge sections. This may result in the multi-lumen design providing conformance in the X, Y and Z directions, due to the flexibility of lumen hinge sections between each lumen. This design allows effective and feasible conformance to a variety of different users teeth and gum topography, providing the effective gum sealing without irritating the gums and allowing dynamic positioning of the liquid cleaning jets around each of the teeth to obtain proximal and interdental cleaning action. The multiple lumens are also attached to the first fluid manifold 1162 and second fluid manifold 1164. This creates a secondary flexible joint providing two additional degrees of motion for the adjusting to different bite architectures that may be encountered.

The proximal sealing membrane 1152 and distal sealing membrane 1154 provide a flexible and universal sealing mechanism to minimize leakage into the oral cavity while redirecting flow onto and around teeth, to maximize treatment/cleaning area to get to hard-to-reach-places (HTRP). The membrane can provide an elastic function across the lumen longitudinal axis to form around the teeth and gums.

Lumens 1156*a*, 1156*b*, 1156*c*, 1157*a*, 1157*b*, and 1157*c* provide the flexibility required for effective fit or sealing within the oral cavity and allowing redirection and flow of fluids back towards the teeth and/or gingival surfaces.

In one embodiment of a cleaning operation, cleaning liquid is pumped through first fluid channel 1142, and enters first fluid manifold 1162 through first manifold feed 1146. Liquid enters first liquid lumens 1156*a*, 1156*b*, and 1156*c* from first fluid manifold 1162. The cleaning liquid then enters LCC 1160 through first nozzles 1166. A vacuum is pulled on second manifold feed 1148 (not shown) to pull the cleaning liquid through second nozzles 1168 (not shown), into second liquid lumens 1157*a*, 1157*b*, and 1157*c*. The liquid enters second fluid manifold 1164, then flows through second manifold feed 1148, and finally into second fluid channel 1144.

In this embodiment, jets of cleaning liquid are first directed from first fluid manifold 1162 to the first surfaces of the teeth and/or gingival area from one side of LCC 1160, and directed through, between, and around the surfaces of the teeth and/or gingival area from the other side of the LCC into the second fluid manifold 1164 to provide controlled interdental, gumline, surface and/or gingival area cleaning or treatment.

Next, the flow in the manifolds is reversed. Cleaning liquid is pumped through second fluid channel 1144, second fluid manifold 1164 through second manifold feed 1148. Liquid enters second liquid lumens 1157*a*, 1157*b*, and 1157*c* from second fluid manifold 1164. The cleaning liquid then enters LCC 1160 through second nozzles 1168. A vacuum is pulled on first manifold feed 1146 to pull the cleaning liquid through first nozzles 1166, into first liquid lumens 1156*a*, 1156*b*, and 1156*c*. The liquid enters first fluid manifold 1162, then flows through first manifold feed 1146, and finally into first fluid channel 1142.

In the second portion of this embodiment, jets of cleaning liquid are directed onto the second surfaces of the teeth and/or gingival area, and directed through, between, and around surfaces of the teeth and/or gingival area. The alternating of pressure/vacuum through a number of cycles creates a turbulent, repeatable and reversible flow to provide reciprocation of liquid about the plurality of surfaces of the oral cavity to substantially simultaneously contact the surfaces of the oral cavity with liquid, thereby providing the desired beneficial effect.

In another embodiment it may be preferable to deliver the liquid through both manifolds simultaneously, flooding LLC 1160, submerging the teeth for a period of time and then evacuating LCC 1160 after a set period of time through one or both manifolds. Here, cleaning or treating liquid is simultaneously pumped through first fluid channel 1142 into first fluid manifold 1162 via first manifold feed 1146, and through second fluid channel 1144 into second fluid manifold 1164 via second manifold feed 1148. Liquid then simultaneously enters first liquid lumens 1156*a*, 1156*b*, and 1156*c* from first fluid manifold 1162, and second liquid lumens 1157*a*, 1157*b*, and 1157*c* from second fluid manifold 1164. The cleaning liquid then enters LCC 1160 simultaneously through first nozzles 1166 and second nozzles 1168. To evacuate LCC 1160, a vacuum is simultaneously pulled on first manifold feed 1146 through first fluid channel 1142, and second manifold feed 1148 through second fluid channel 1144. Cleaning or treatment liquid is simultaneously pulled through first nozzles 1166 and second nozzles 1168, into first manifold feed 1146 and second manifold feed 1148.

It is also possible to deliver different liquid compositions to first manifold feed 1146 and second manifold feed 1148. The different liquid compositions would then combine in LCC 1160 for improved cleaning efficacy or treatment effects. In the dual manifold design it may be preferable to supply each manifold from a separate liquid supply reservoir, such as in a dual action piston pump configuration, where one supply line connects to supply first manifold feed 1146 and the other piston supply line provides and removes liquid from second manifold feed 1148, e.g. when one manifold is being supplied with liquid the second manifold is removing liquid, and vice versa.

In other embodiments, valves can be placed at the entry to first liquid lumens 1156*a*, 1156*b*, and 1156*c*, or at the entry to second liquid lumens 1157*a*, 1157*b*, and 1157*c* to provide improved function by allowing lumens to engage at different times (at different points in the cleaning/treatment cycle), at pulsed intervals. As an example, in one embodiment, not all lumens engage in the liquid pumping/vacuum function. Here, first liquid lumen 1156*a* and second liquid lumen 1157*a*, which primarily engage the gums, only engage in the liquid vacuum function. This would help prevent liquid from leaking into the oral cavity. Valving also allows for variable flow, allowing a decreased resistance to the liquid vacuum function, or allowing increased pumping, and therefore liquid velocity, during liquid delivery.

In still other embodiments, individual inner first nozzles 1166 or second nozzles 1168 may have integrated one-way valves, such as duckbill valves or umbrella valves, to allow flow only in one direction out of those particular nozzles. This may be effective to increase vacuum relative to pressure/delivery in LCC 1160.

Manufacturing of the multi-lumen design for the cleaning component 1150 m utilizing existing available manufacturing and assembly processes such as extrusion, injection, vacuum, blow, or compression molding. Other feasible techniques include rapid prototyping techniques such as 3D printing and other additive techniques, as well as subtractive techniques.

One manufacturing method is to create individual component shells through vacuum forming. Low cost methods allow vacuuming forming of very thin wall structures. The component geometry is designed to provide the interlocking features and structural geometry to allow minimization of the size of cleaning component 1150. When assembled, the manufactured components form the necessary manifolds and flow structure (bidirectional and/or dedicated manifolds) to provide the required performance characteristics for treating/cleaning the teeth.

Materials for the lumens could range from lower durometer flexible materials (25 shore A) to harder materials more rigid materials (90 shore A), preferably being between 30 and 70 shore A.

Materials could be silicone, thermoplastic elastomer (TPE), polypropylene (PP), polyethylene (PE), polyethylene terephthalate (PET), ethylene vinyl acetate (EVA), polyurethane (PU), or multi-component (combination of materials and hardness) to achieve desired design and performance attributes.

The first nozzles 1166 and second nozzles 1168 could be made through a secondary operation such as drilling or punching, or formed during molding. Alternatively, the first nozzles 1166 and second nozzles 1168 could be inserted into cleaning component 1150 to provide increased wear and or different jet performance characteristics, and could be combined with frictional cleaning elements or other components to enhance the cleaning and/or treatment affect.

Figure 14:
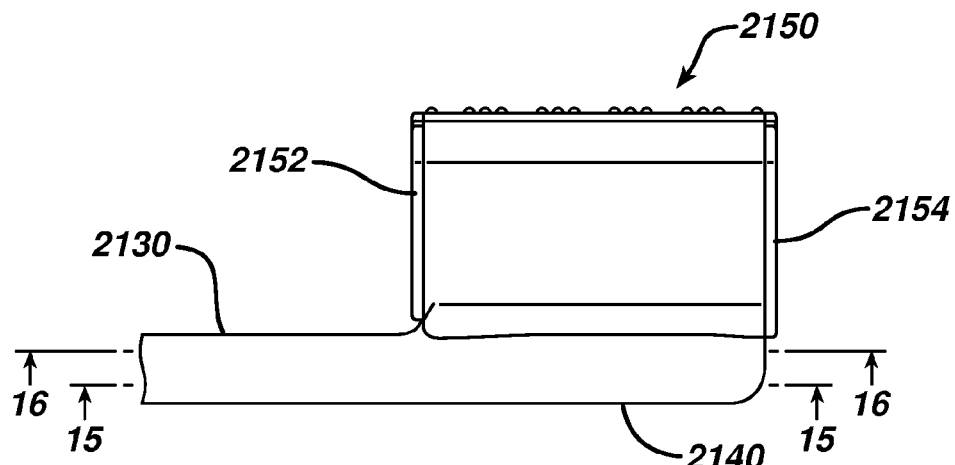
FIG. 14 is a side view of the neck and head of a third embodiment of an applicator device according to the present invention.
Figure 15:
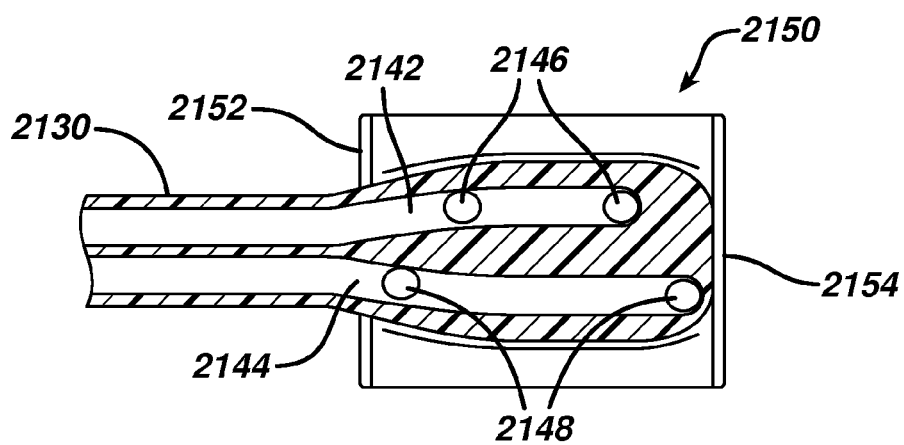
FIG. 15 is a horizontal sectional view of FIG. 14 along the 15-15 plane.
Figure 16:
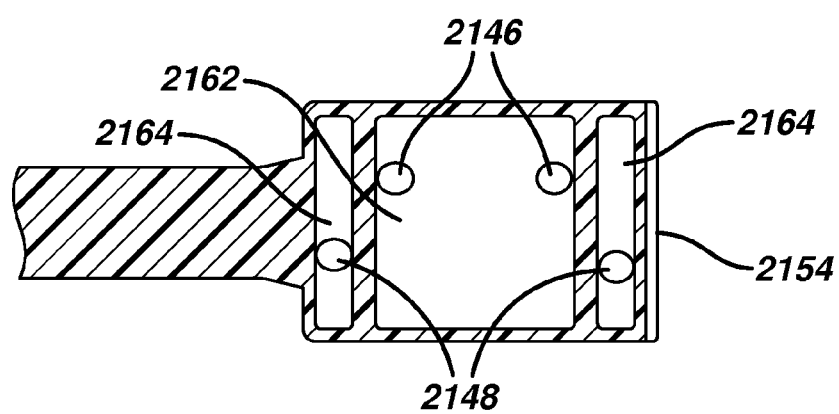
FIG. 16 is a horizontal sectional view of FIG. 14 along the 16-16 plane.

Although the embodiment of FIGS. 12 and 13 show a single cleaning component 1150 on head 1140, it is to be understood that a second cleaning component similar to cleaning component 1150 may be disposed on the opposite facing of head 1140. The second cleaning component would provide substantially simultaneous contact of a plurality of surfaces of both top and bottom sections of the oral cavity FIGS. 14 to 20 show a third embodiment of application device according to the present invention. FIG. 14 is a side view of neck 2130 and head 2140 of the device. The figure shows cleaning component 2150 disposed on the facing of head 2140. The figures show cleaning component 2150 is comprised of proximal sealing membrane 2152, distal sealing membrane 2154, first side wall 2156a, second side wall 2156b, and base inner wall 2158. FIG. 15 is a horizontal sectional view of FIG. 14 along the 15-15 plane. The figure shows delivery channel 2142 and vacuum channel 2144 disposed in neck 2130 and head 2140. Delivery manifold feed 2146 connects delivery channel 2142 to delivery manifold 2162 in cleaning component 2150. Vacuum manifold feed 2148 connects vacuum channel 2144 to vacuum manifold 2164 in cleaning component 2150. FIG. 16 is a horizontal sectional view of FIG. 14 along the 16-16 plane. The figure shows delivery manifold feed 2146 connected to delivery manifold 2162, and vacuum manifold feed 2148 connected to vacuum manifold 2162.

Figure 17:
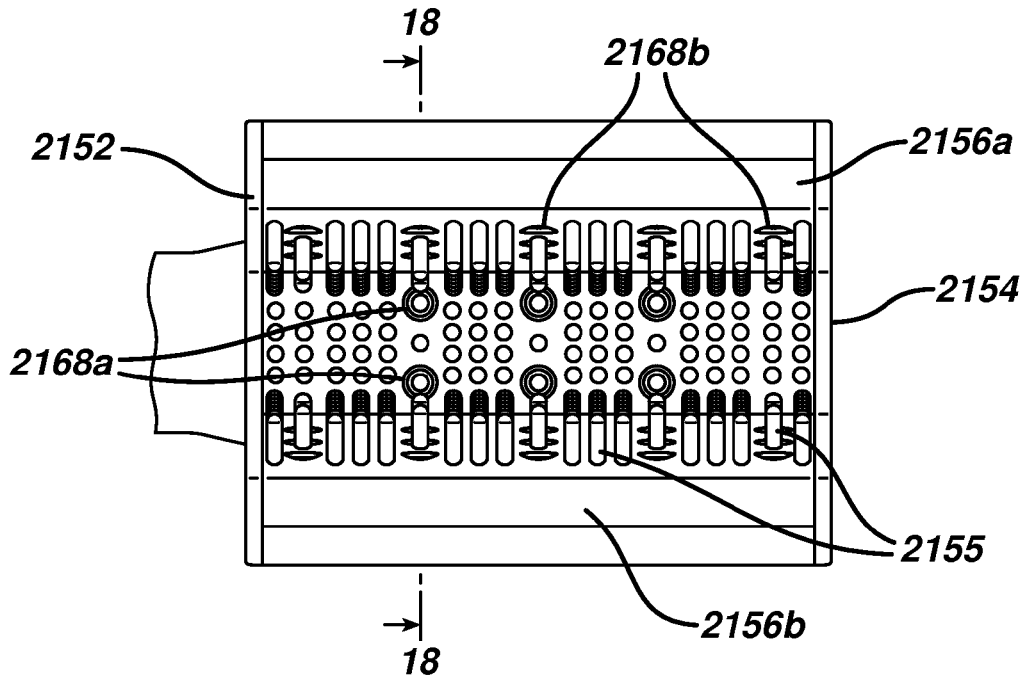
FIG. 17 is a top view of the head portion of the embodiment of the device of FIG. 14.

FIGS. 17 through 20 are views of cleaning component 2150. FIG. 17 is a top view of cleaning component 2150, including proximal sealing membrane 2152, distal sealing membrane 2154, cleaning elements 2155, first side wall 2156a, second side wall 2156b, and base inner wall 2158. Though the figures show cleaning elements 2155 located on first side wall 2156a, second side wall 2156b, and base inner wall 2158, cleaning elements 2155 may be located on only one wall (2156a, for example), or on any combination of side walls (2156a and 2156b) and base inner wall 2158 in other embodiments. In addition, the shape, size, number and layout of cleaning elements 155 may be optimized for improved cleaning.

Figure 18:
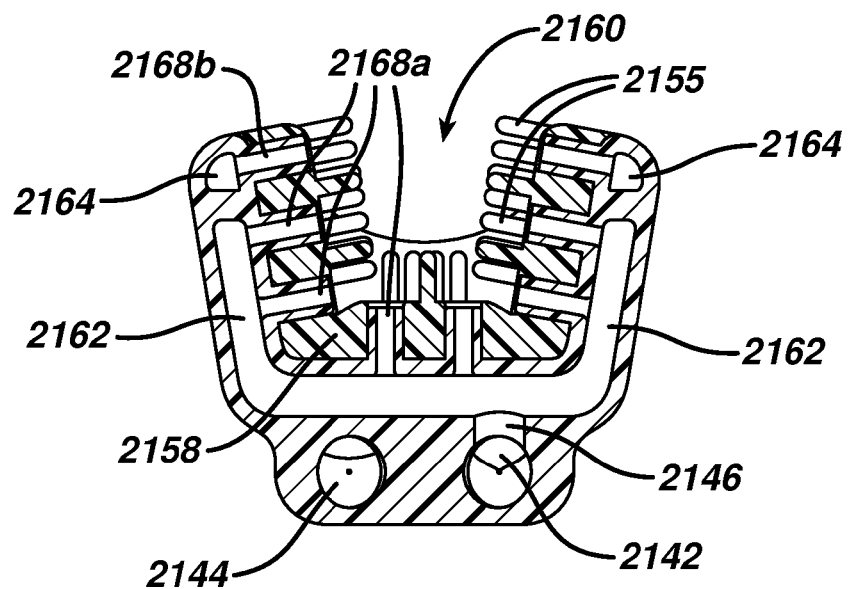
FIG. 18 is a vertical sectional view of FIG. 17 along the 18-18 plane.

FIG. 18 is a vertical sectional view of FIG. 17 along the 18-18 plane. The figure shows liquid-contacting chamber (LCC) 2160, defined by proximal sealing membrane 2152, distal sealing membrane 2154, first side wall 2156a, second side wall 2156b, and base inner wall 2158. The figure also shows that delivery channel 2142 connects to delivery manifold feed 2146, which connects to delivery manifold 2162. Though not shown, vacuum channel 2144 connects to vacuum manifold feed 2148, which connects to vacuum manifold 2164. Fluid exits delivery manifold 2162 through delivery nozzles 2168a. Fluid enters vacuum manifold 2164 through vacuum nozzles 2168b.

Figure 19:
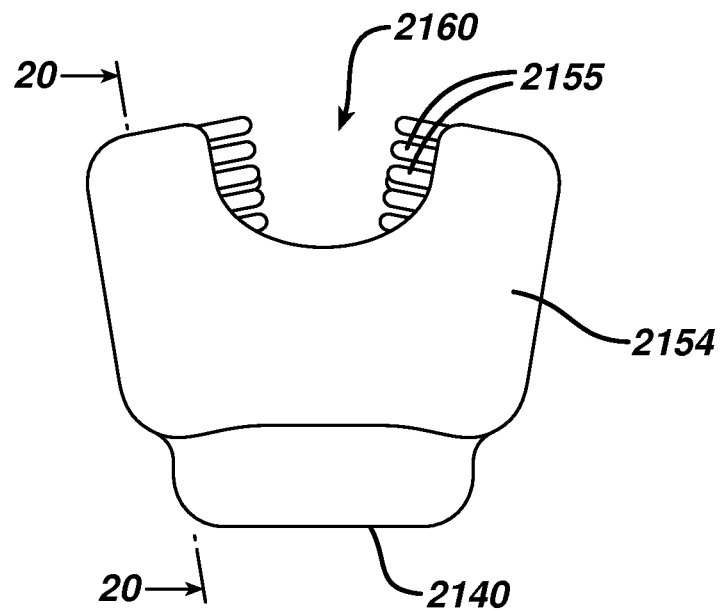
FIG. 19 is an end view of the head portion of the embodiment of the device of FIG. 14.
Figure 20:
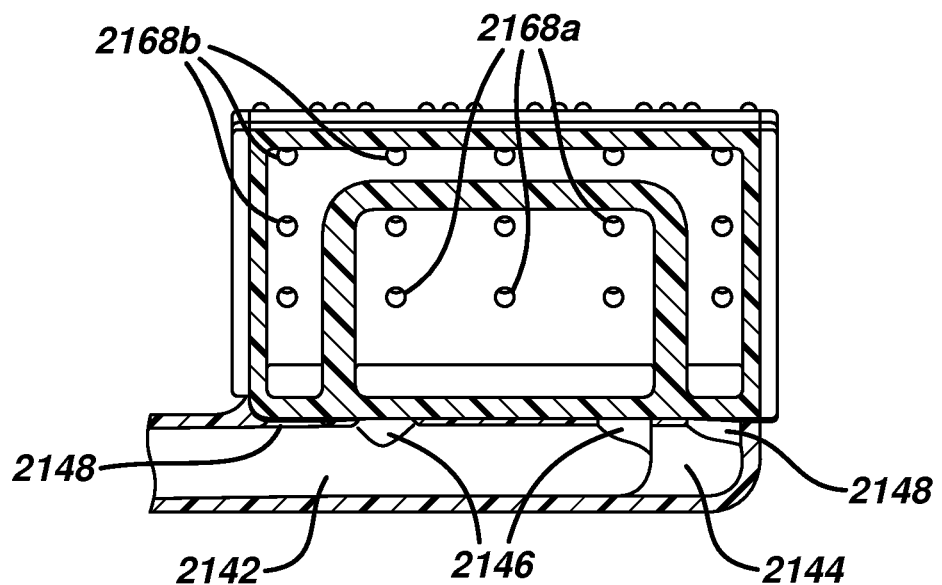
FIG. 20 is a vertical sectional view of FIG. 19 along the 20-20 plane.

FIG. 19 is an end view of cleaning component 2150. FIG. 20 is a vertical sectional view of FIG. 19 along the 20-20 plane. The figures show delivery channel 2142 connected to delivery manifold feeds 2146, which are connected to delivery manifold 2162 in cleaning component 2150. Delivery manifold 2162 feeds delivery nozzles 2168a. Vacuum channel 2144 is connected to vacuum manifold feeds 2148, which are connected to vacuum manifold 2164 in cleaning component 2150. Vacuum manifold 2164 draws fluid from vacuum nozzles 2168b.

FIG. 20 shows delivery nozzles 2168a located in the central region of cleaning component 2150, while vacuum nozzles 2168b are located peripherally to delivery nozzles 2168a. This nozzle layout is expected to result in a consistent flow of cleaning fluid through the LCC 2160. It is to be understood that in the layout of delivery nozzles 2168a and vacuum nozzles 2168b are only one embodiment of nozzle configuration. The layout of the nozzles, as well as the geometry of the nozzle openings may change.

The proximal sealing membrane 2152 and distal sealing membrane 2154 provide a flexible and universal sealing mechanism to minimize leakage into the oral cavity while redirecting flow onto and around teeth, to maximize treatment/cleaning area to get to hard-to-reach-places (HTRP). The membrane can provide an elastic function across the lumen longitudinal axis to form around the teeth and gums.

Base inner wall 2158 provides the flexibility required for effective fit or sealing within the oral cavity and allowing redirection and flow of fluids back towards the teeth and/or gingival surfaces.

In one embodiment of a cleaning operation, cleaning liquid is pumped through delivery channel 2142, and enters delivery manifold 2162 through delivery manifold feed 2146. The cleaning liquid then enters LCC 2160 through delivery nozzles 2168a. A vacuum is pulled on vacuum manifold feed 2148 to pull the cleaning liquid through vacuum nozzles 2168b, into vacuum manifold 2164, then flows through vacuum manifold feed 2148, and finally into vacuum channel 2144.

In this embodiment, jets of cleaning liquid are simultaneously directed from delivery manifold 2162 to both surfaces of the teeth and/or gingival area in LCC 2160 to provide controlled gumline, surface and/or gingival area cleaning or treatment.

In another embodiment it may be preferable to deliver the liquid through both manifolds simultaneously, flooding LCC 2160, submerging the teeth for a period of time and then evacuating LCC 2160 after a set period of time through one or both manifolds. Here, cleaning or treating liquid is simultaneously pumped through delivery channel 2142 and vacuum channel 2144. Liquid will enter LCC 2160 simultaneously through delivery nozzles 1268a and vacuum nozzles 1268b. To evacuate LCC 2160, a vacuum is simultaneously pulled on delivery channel 2142 and vacuum channel 2144. Cleaning or treatment liquid is simultaneously pulled through delivery nozzles 1268a and vacuum nozzles 1268b.

Although the embodiment of FIGS. 14 through 20 show a single cleaning component 2150 on head 2140, it is to be understood that a second cleaning component similar to cleaning component 2150 may be disposed on the opposite facing of head 2140. The second cleaning component would provide substantially simultaneous contact of a plurality of surfaces of both top and bottom sections of the oral cavity FIGS. 21 to 27 show a fourth embodiment of an application device according to the present invention. FIG. 21 is a right side front perspective view of the neck and head of this embodiment. The figure shows neck 2530 and head 2540 of the device. Cleaning component 2550 is disposed on the facing of head 2540. Cleaning component 2550 is comprised of sealing membranes 2552 on the proximal and distal ends of cleaning component 2550, first side wall 2556a, second side wall 2556b, and base wall 2558. Cleaning elements 2555 are disposed on the first side wall 2556a, second side wall 2556b, and base wall 2558. Spray nozzles 2568 are disposed on the distal end of a number of the cleaning elements 2555 located on the first side wall 2556a and second side wall 2556b of cleaning component 2550. It is important to note that in other embodiments spray nozzles 2568 may be disposed on any of the first side wall 2556a, second side wall 2556b, base wall 2558, or at the distal end of some or all of the cleaning elements 2555 located on any or all of the walls of cleaning component 2550. The figure also shows liquid-contacting chamber (LCC) 2560, defined by sealing membranes 2552, first side wall 2556a, second side wall 2556b, and base wall 2558.

FIGS. 22 and 23 are exploded views of the embodiment of the device of FIG. 21. FIG. 22 is a right side front exploded view, while FIG. 23 is a left side bottom exploded view. Each figure shows neck 2530, head 2540, and cleaning component 2550 of the device. FIG. 22 shows manifold feeds 2546 and 2548, as well as head pivot hole 2545 on the top surface of head 2540. FIG. 23 shows head pivot hole 2545 on the bottom surface of head 2540, as well as manifold entry slots 2551 and 2557, cleaner pivot hole 2553 and rotation groove 2554 on the bottom surface of cleaning component 2550. Manifold feeds 2546 and 2548 are aligned with manifold entry slots 2551 and 2557, so as to create paths for fluid flow and vacuum flow from first channel 2542 and second channel 2544. As cleaning component 2550 rotates about pivot holes 2545 and 2553, manifold feeds 2546 and 2548 switch alignment with manifold entry slots 2551 and 2557. Accordingly, cleaning component 2250 may pivot, i.e. is rotatable, around the horizontal and longitudinal axis of head 2540. Though not shown, a gasket may be placed in rotation groove 2554 to prevent leakage as cleaning component 2550 rotates about the top surface of head 2540. Also not shown in the figures is a pin which is disposed in pivot holes 2545 and 2553. This allows rotation of cleaning component 2550 on the top surface of head 2540.

Figure 24:
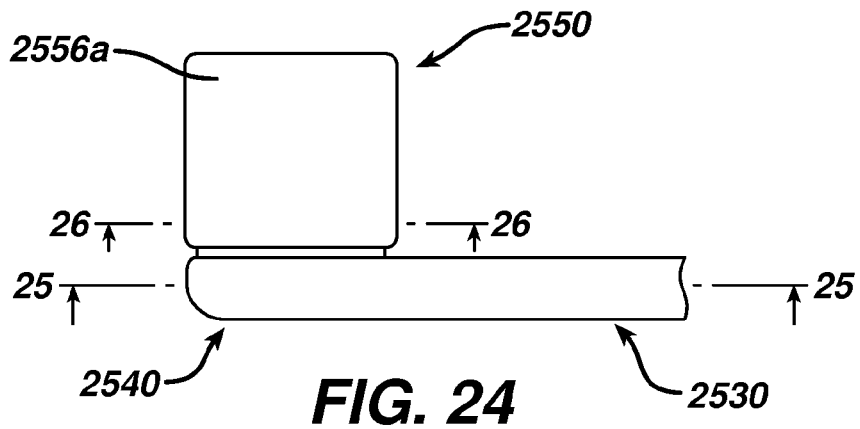
FIG. 24 is a side view of the neck and head of the embodiment of the device of FIG. 21.
Figure 25:
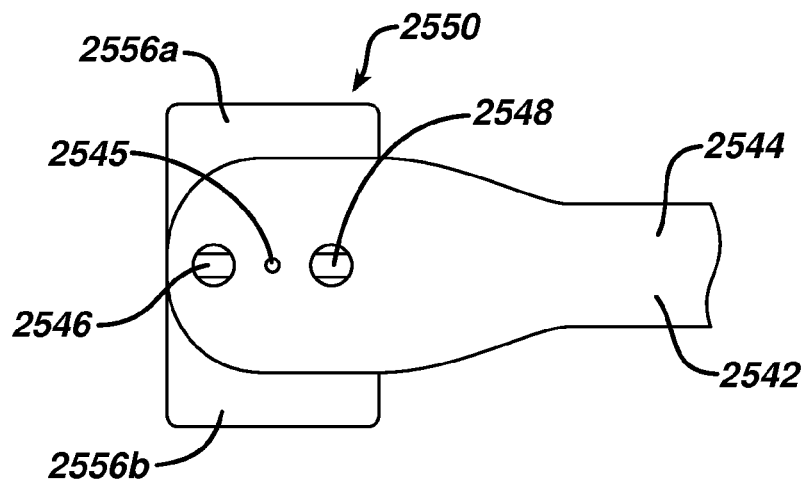
FIG. 25 is a horizontal sectional view of FIG. 21 along the 25-25 plane.
Figure 26:
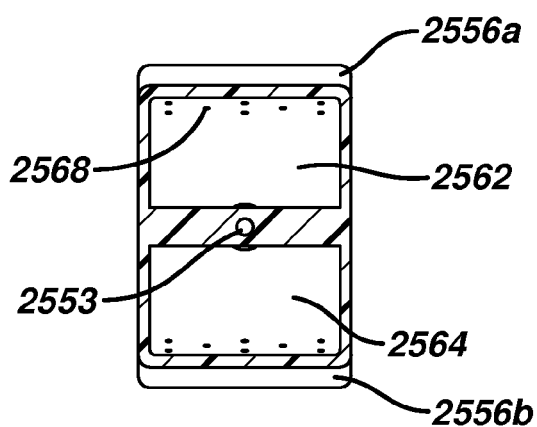
FIG. 26 is a horizontal sectional view of FIG. 21 along the 26-26 plane.

FIG. 24 is a side view of neck 2530 and head 2540 of the device of FIG. 21. The figure shows cleaning component 2550 disposed on the facing of head 2540. FIG. 25 is a horizontal sectional view of FIG. 24 along the 25-25 plane. The figure shows first channel 2542 and second channel 2544 disposed in neck 2530 and head 2540. First manifold feed 2546 and second manifold feed 2548 connects first channel 2542 and second channel 2544, respectively, to first manifold 2562 or second manifold 2564 in cleaning component 2550. FIG. 26 is a horizontal sectional view of FIG. 24 along the 26-26 plane. The figure shows first manifold 2562 and second manifold 2564.

Figure 27:
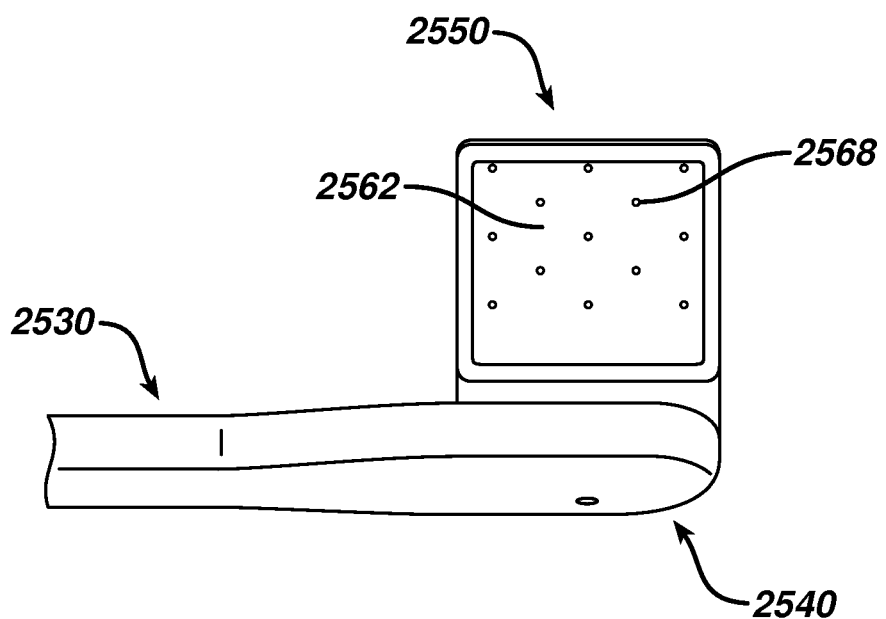
FIG. 27 is a vertical sectional view of FIG. 21 along the 27-27 plane.

FIG. 27 is a vertical sectional view of FIG. 21 along the 27-27 plane. The figure shows first manifold 2562 of cleaning component 2550. Spray nozzles 2568 are disposed on the first side wall 2556a of cleaning component 2550.

In one embodiment of a cleaning operation, cleaning liquid is pumped through first channel 2542, and enters first manifold 2562 through first manifold feed 2546. The cleaning liquid then enters LCC 2560 through spray nozzles 2568 located on the distal end of cleaning elements 2555 disposed on the first side wall 2556a. A vacuum is pulled on second manifold feed 2548 to pull the cleaning liquid through vacuum nozzles 2168 located on the distal end of cleaning elements 2555 disposed on the second side wall 2556b into vacuum manifold 2564. The fluid then flows through second manifold feed 2548, and finally into second channel 2544.

Figure 28:
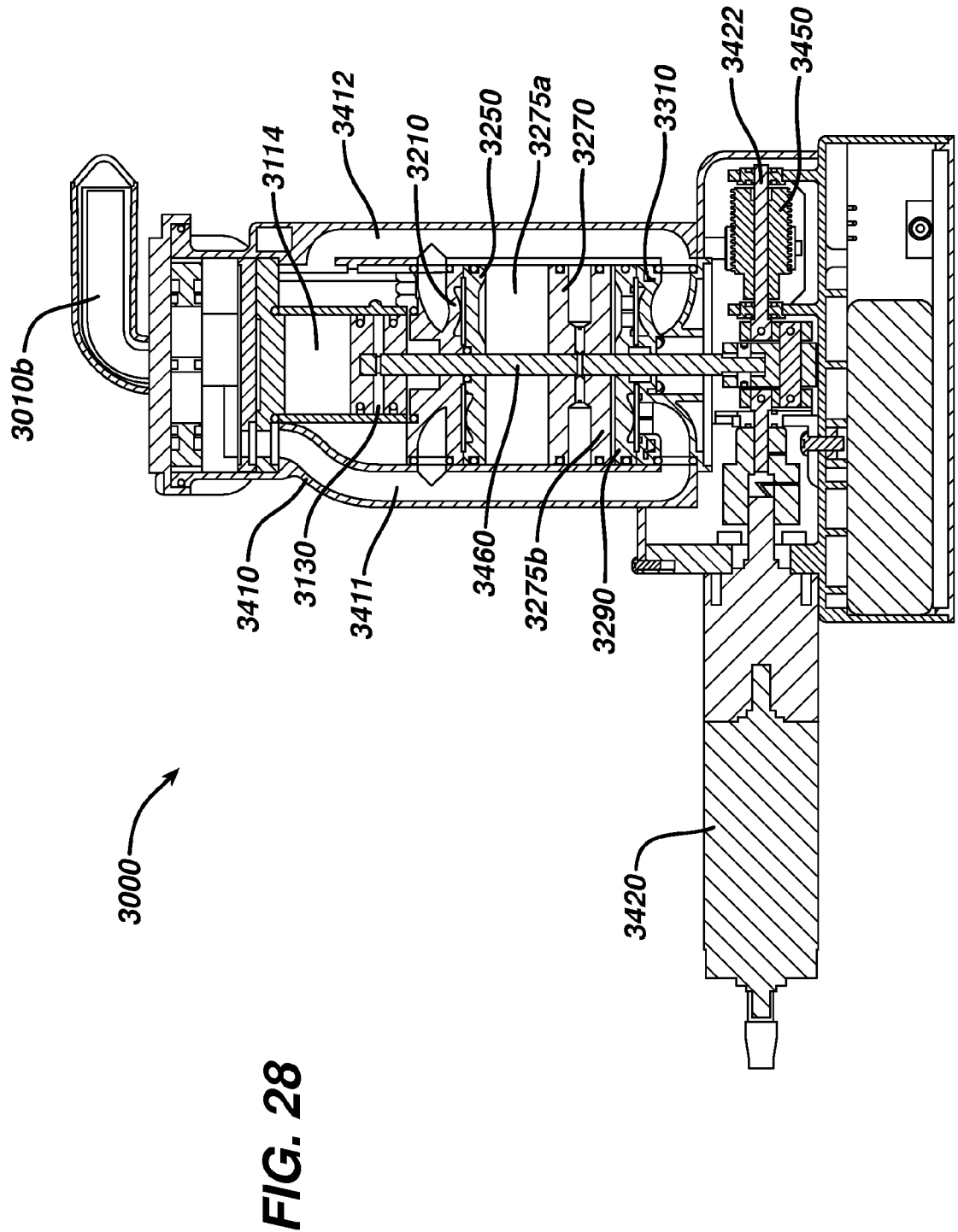
FIG. 28 is a cut-away view of a base unit with which an applicator device of the present invention may be used.

An embodiment of a base unit used with devices according to the present invention is shown in FIG. 28. FIG. 28 is a cut-away view of device 3000, showing the spatial relationships between the components in the pumping section, vacuum section, and pumping and driving sections. Cylinder volume 3412 is the volume of vacuum cylinder sleeve 3410 not occupied by the components of the pumping section, vacuum section, and pumping and driving sections, and serves as the liquid reservoir in the embodiment shown. The general operation of device 3000 is as follows:

Device 3000 is sufficiently filled with cleaning liquid. The liquid initially resides in cylinder volume 3412 of vacuum cylinder sleeve 3410. The user inserts any embodiment of a liquid applicator according to the present invention into their mouth. Device 3000 may be activated by a sensor (pressure sensor, proximity sensor, etc.) or the device may be activated by the user. The cleaning cycle is initiated.

On the "down stroke" of piston rod 3460, delivery piston 3130 pulls liquid from the bottom of cylinder volume 3412 into delivery volume 3114.

On the "upstroke" of piston rod 3460, delivery piston 3130 forces the liquid through base port 742 of reciprocating flow controller 710. Liquid flow through reciprocating flow controller 710 is described earlier using FIG. 3c and FIG. 3d. In brief, when reciprocating flow controller 710 in its first position (FIG. 3c), incoming liquid from delivery volume 3114 enters reciprocating flow controller 710 through base port 742. The liquid exits reciprocating flow controller 710 through cap port 722, flowing into outlet pipe 3010b. Returning liquid, flowing in through outlet pipe 3010a (not shown), reenters reciprocating flow controller 710 through cap port 724. The liquid exits reciprocating flow controller 710 through base port 744. When reciprocating flow controller 710 in its second position (FIG. 4d), incoming liquid from delivery volume 3114 enters reciprocating flow controller 710 through base port 742. The liquid exits reciprocating flow controller 710 through cap port 724, flowing into outlet pipe 3010a. Returning liquid, flowing in through outlet pipe 3010b, reenters reciprocating flow controller 710 through cap port 722. The liquid re-exits reciprocating flow controller 710 through base port 744. Reciprocation of cleaning liquid in applicator 100 of FIG. 1 is achieved by switching reciprocating flow controller 710 between its first and second positions. The switching of reciprocating flow controller 710 between its first and second positions is achieved by a worm gear, which is linked to position adjuster 732 in reciprocating flow controller 710. Though shown as continually rotating in this embodiment, it is to be understood that reciprocating flow controller 710 may be driven via separate means, such as another motor. Also, the time interval for switching reciprocating flow controller 710 between its first and second positions may, in some embodiments be between about 1 and about 100 seconds, or between about 2 and about 10 seconds, and may be varied over the course of the cleaning/treatment.

In the present embodiment, the vacuum section of device 3000 is effective during both the "upstroke" and "down stroke" of piston rod 3460. Vacuum piston 3270 is dual acting, and draws liquid from liquid applicator 100 on both the upstroke and down stroke of vacuum piston 3270. The liquid flowing through base port 744 of reciprocating flow controller 710 flows through vacuum volumes 3275a or 3275b. Vacuum volume 3275a is the volume between vacuum end disk 3250 and vacuum piston 3270. Vacuum volume 3275b is the volume between vacuum end disk 3290 and vacuum piston 3270. During the "upstroke" of piston rod 3460, the liquid in base port 744 is drawn into vacuum volume 3275b and simultaneously expelled from vacuum volume 3275a into cylinder volume 3412. During the "down stroke" of piston rod 3460, the liquid in base port 744 is drawn into vacuum volume 3275a and simultaneously expelled from vacuum volume 3275b into cylinder volume 3412. As noted, the vacuum piston 3270 in this embodiment is dual acting, drawing liquid from applicator 100 on both the upstroke and down stroke of vacuum piston 3270. So, while vacuum volume 3275b is drawing in liquid from base port 744, the liquid in vacuum volume 3275a is being pumped into cylinder volume 3412. In contrast, while vacuum volume 3275a is drawing in liquid from base port 744, the liquid in vacuum volume 3275b is being pumped into cylinder volume 3412. During the "upstroke" of piston rod 3460, the liquid in vacuum volume 3275a is pumped into cylinder volume 3412. During the "down stroke" of piston rod 3460, the liquid in vacuum volume 3275b is pumped into cylinder volume 3412.

The cycle continues with cycles comprising both "upstrokes" and "down strokes" of piston rod 3460, with liquid motion through device 3000 as above.

The ratio of the total volume of vacuum volumes 3275a and 3275b to delivery volume 3114 may be any range, such as 1:1, optionally about 3:1 or greater, or about 4:1 or greater. Since delivery piston 3130 only delivers liquid on one "half" of the pumping/vacuuming cycle, while vacuum piston 3270 works on both halves of the cycle. The dual acting vacuum piston 3270 also provides vacuum during the half of the stroke where delivery piston 3130 is not delivering liquid, increasing the opportunity to retrieve liquid from applicator 100, as well as clear additional liquid which leaked from liquid applicator 100 into the oral cavity. Testing has shown a minimum 3:1 volumetric ratio of liquid vacuum to liquid delivery per stroke provided the necessary vacuum to minimize leakage into the oral cavity from liquid applicator 100 when the applicator has a marginal gingival seal, which may occur in embodiments of a universal (designed to fit a range of people) liquid applicator 100 design.

In some embodiments vacuum piston 3270 is single acting. However, a dual acting vacuum piston 3270 may show some advantages.

In some embodiments, cylinder volume 3412 may have an air separator to reduce the foaming. Also, a breather vent may be required so that the pumping/vacuum system does not over pressurize and lock/fail. There may be a wall to split the cylinder volume 3412 into two halves, to further reduce the chance of liquid splashing out of the breather vent.

In general, cylinder volume 3412 is vented since more liquid is being delivered to cylinder volume 3412 from the vacuum system than is being drawn from the delivery system. The excess (air) is exhausted from a vent in cylinder volume 3412. The vent could use a valve, such as an umbrella valve, so air can escape but cannot enter the reservoir from the same opening, or a 2-way valve or vent hole. To further reduce loss of liquid through the vent, a wall may be used to divide cylinder volume 3412 in two parts. One side contains the supply line, and the other side contains the vent. To optimize the separation of air from liquid in cylinder volume 3412, an air separator may be placed in the reservoir, below the supply line. As the liquid drops from supply line into cylinder volume 3412, it passes through an air separator, which may be a solid plate with holes. This allows the liquid to pass, while removing entrained air and helping to separate the two liquid states (liquid vs. gas). The air separator may have various designs, such as an angled solid shelf with holes, a spiraling ramp, a spiraling ramp with holes, two or more levels of angled shelves with holes, multiple spiraling ramps, similar to a multiple starting points for threads, (bottle caps, etc), sporadically located bosses that the liquid hits as it drops, assisting in separation.

In one embodiment, the base unit be a self-contained, portable unit with a rechargeable battery, have a motor-driven piston pump for liquid delivery, have a mechanism to control the liquid flow, keep the temperature within a specified range, be modular in design, and have ergonomics well-suited to the user's hand. When the hand piece is in the base station, it will recharge the battery, refill the liquid reservoirs in the hand piece from those in the base station, and exchange samples and/or diagnostic information with the base station. It may also go through a cleaning process.

What is claimed is:

1. A device for directing a liquid onto a plurality of surfaces of an oral cavity of a mammal, said device comprising:
   a handle, comprising;
      first and second ports for receiving said liquid in said handle, said first and second ports located at a proximal end of said handle; and
      first and second channels for transporting said liquid, said first and second channels connected to said first and second ports at said proximal end of said handle and extending longitudinally through said handle;
   a neck, comprising;
      said first and second channels for transporting said liquid extending longitudinally through said neck; and
   a head, comprising:
      a cleaning component, said cleaning component comprising a chamber for maintaining said liquid proximate said plurality of surfaces, said chamber defined by proximal and distal sealing membranes, first and second inner side walls extending longitudinally between said proximal and distal sealing membranes, and a base inner wall extending horizontally between said first and second inner side walls and longitudinally between said proximal and distal sealing membranes, said first and second inner side walls comprising a plurality of openings,
      a first manifold for containing a first portion of said liquid and providing said first portion to said chamber through said openings of said first inner side wall,
      a second manifold for containing a second portion of said liquid and providing said second portion to said chamber through said openings of said second inner side wall,
      a first manifold feed for conveying said first portion of liquid to and/or from said first manifold; and
      a second manifold feed for conveying said second portion of liquid to and/or from said second manifold
      wherein said cleaning component is rotatable around a horizontal and longitudinal axis of said head.

2. The device of claim 1 further comprising means for attaching said device to means for providing said liquid to said device.

3. The device of claim 2 wherein said means for attaching comprises a quick disconnect structure for attaching said device to said means for providing said liquid to said device.

4. The device of claim 1 comprising a plurality of first lumens connected by said first manifold and a plurality of second lumens connected by said second manifold.

5. The device of claim 1 wherein the number, location and cross-sectional geometry of said openings are effective to provide a spray pattern effective to provide a beneficial effect to the oral cavity.

6. The device of claim 5 wherein the cross-sectional geometry of said openings is selected from the group consisting of circular, elliptical and trapezoidal.

7. The device of claim 1 wherein said base inner wall comprises a flexible membrane for providing an effective seal.

8. The device of claim 7 comprising a flexible gum-sealing membrane for providing said effective seal.

* * * * *